United States Patent
Glimcher et al.

(10) Patent No.: US 6,548,734 B1
(45) Date of Patent: Apr. 15, 2003

(54) METHODS RELATING TO MODULATION OF CARTILAGE CELL GROWTH AND/OR DIFFERENTIATION BY MODULATION OF NFATP ACTIVITY

(75) Inventors: Laurie H. Glimcher, West Newton, MA (US); Ann M. Ranger, Brighton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/322,624

(22) Filed: May 28, 1999

Related U.S. Application Data

(63) Continuation-in-part of application No. 09/087,139, filed on May 28, 1998, now abandoned.

(51) Int. Cl.$^7$ .................... G01N 33/00; A01K 67/027; A61K 49/00; C12Q 1/00; C12Q 1/68
(52) U.S. Cl. .................. 800/3; 424/9.1; 424/9.2; 435/4; 435/6; 800/3; 800/13; 800/14; 800/18
(58) Field of Search ............... 800/13, 3, 18; 424/9.1, 9.2; 435/4, 6

(56) References Cited

U.S. PATENT DOCUMENTS 5,672,473 A    9/1997   Glimcher et al. .............. 435/6

FOREIGN PATENT DOCUMENTS

| WO | WO 94/15964 | 7/1994 |
| WO | WO 96/26959 | 9/1996 |
| WO | WO 97/39721 | 10/1997 |

OTHER PUBLICATIONS

K.H.S. Campbell et al., Theriogenology,"Totipotency or multipotentiality of Cultured Cells: Applications and Progress," Jan. 1997, vol. 47, Iss. 1, pp. 63–72.*
A. Bradley et al., Bio/Technology, "Modifying the Mouse: Design and Desire," May 1992, vol. 10, pp. 534–539.*
Aramburu, J. et al. "Selective Inhibition of NFAT Activation by a Peptide Spanning the Calcineurin Targeting Site of NFAT" *Molecular Cell* 1:627–637 (1998).
Eriksson, A.I. et al. "The Management of Chondrosarcoma of Bone" *Clinical Orthopaedics and Related Research* 153:44–66 (1980).
Gyuris, Jeno et al. "Cdi1, A Human G1 and S Phase Protein Phosphatase That Associated With Cdk2" *Cell*, 75:791–803 (1993).
Hodge, M.R. et al. "Hyperproliferation and Dysregulation of IL–4 Expression in NF–ATp–Deficient Mice" *Immunity* 4:397–405 (1996).
Hoey, T. et al. "Isolation of Two New Member of the NF–AT Gene Family and Functional Characterization of the NF–AT Proteins" *Immunity* 2:461–472 (1995).
Lewin, Roger "When Does Homology Mean Something Else?" *Sciences* 237: 1570; (1987).
Masuda, E.S. et al. "NFATx, a Novel Member of the Nuclear Factor of Activated T Cells Family That Is Expressed Predominantly in the Thymus" *Molecular and Cellular Biology* 15(5):2697–2706 (1995).
McCaffrey, P.G. et al. "Isolation of the Cyclosporin–Sensitive T Cell Transcription Factor $NFAT_p$," *Science* 262:750–754 (1993).
Northrop, J.P. et al. "NF–AT Components Define a Family of Transcription Factors Targeted in T–Cell Activation" *Nature* 369:497–502 (1994).
Rao, A. "NF–ATp: A Transcription Factor Required for the Co–ordinate Induction of Several Cytokine Genes" *Immunology Today* 15:274–281 (1994).
Riley, James L. et al. "Activation of Class II MHC Genes Requires Both The X Box Region and the Class II Transactivator (CIITA)" *Immunity*, 2:533–543 (1995).
van Loon, C.J.M. et al. "Chondrosarcoma of Bone: Oncologic and Functional Results" *Journal of Surgical Oncology* 57:214–221 (1994).
Xanthoudakis, S. et al. "An Enhanced Immune Response in Mice Lacking the Transcription Factor NFAT1" *Science* 272:892–895 (1996).
Zhou, Hong and Glimcher, Laurie "Human MHC Class II gene Transcription Directed By The Carboxyl Terminus Of CIITA, One of the Defective Genes In Type II MHC Combined Immune Deficiency" *Immunity* 2:545–553. (1995).

* cited by examiner

*Primary Examiner*—Anne-Marie Baker
(74) *Attorney, Agent, or Firm*—Lahive & Cockfield, LLP; Giulio A. DeConti, Jr., Esq.; Cynthia L. Kanik

(57) ABSTRACT

The invention demonstrates that NFATp represses cartilage cell division and represses the chondrogenic program in cells and displays the properties of a tumor suppressor gene. In addition, the invention demonstrates that inhibition of NFATp activity promotes cartilage cell proliferation and differentiation. Methods for identifying modulators of cartilage growth and/or differentiation, using either NFATp-deficient cells or NFATp-containing indicator compositions, are provided. Methods of modulating cartilage cell growth and/or differentiation using agents that modulate the activity of NFATp are also provided. Methods for diagnosing disorders associated with aberrant cartilage cell growth and/or differentiation, by assessing a change in NFATp expression, are also provided.

16 Claims, 8 Drawing Sheets

NFATp -/- Chondroblasts Proliferate Even When Confluent

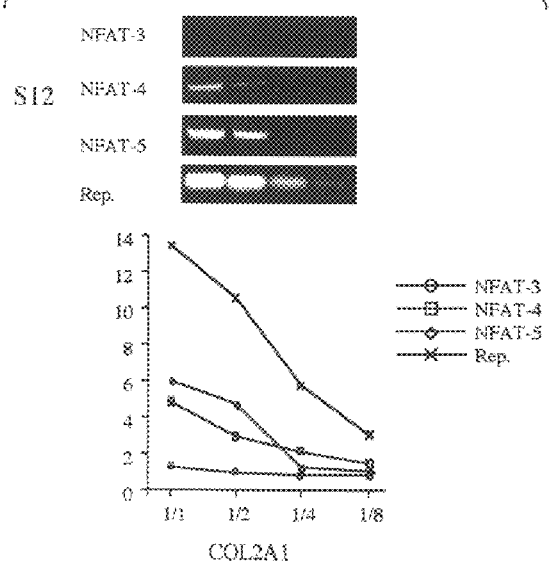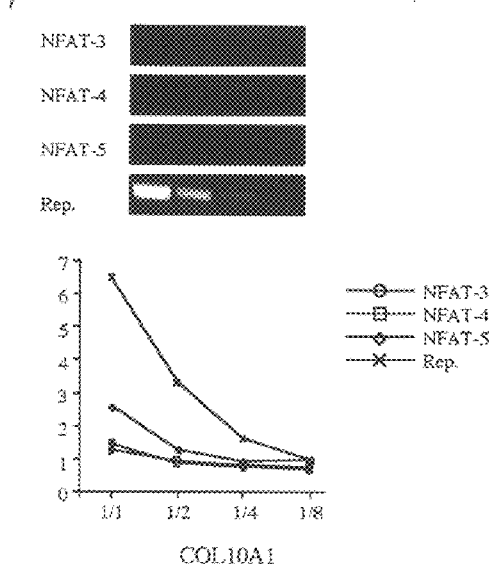

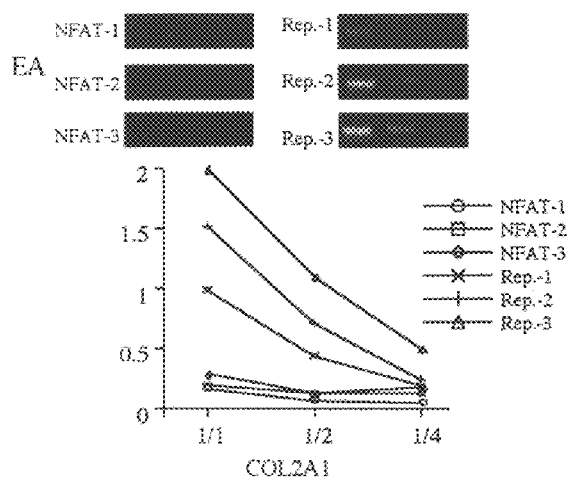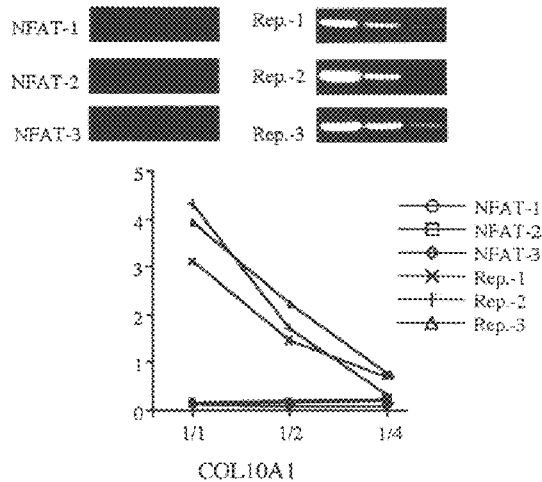
FIG. 5E
FIG. 5F

METHODS RELATING TO MODULATION OF CARTILAGE CELL GROWTH AND/OR DIFFERENTIATION BY MODULATION OF NFATP ACTIVITY

RELATED APPLICATIONS

This application is a continuation-in-part of and claims priority to U.S. Ser. No. 09/087,139, filed on May 28, 1998, now abandoned, incorporated herein in its entirety by this reference.

GOVERNMENT FUNDING

Work described herein was supported, at least in part, under grants AI/AG37833, HD22400, and AG14701, awarded by the National Institutes of Health. The U.S. government therefore may have certain rights in this invention.

BACKGROUND OF THE INVENTION

The NFAT (nuclear factor of activated T cells) family comprises several structurally related proteins that are encoded by at least four distinct genes (see e.g., McCaffrey et al. (1993) *Science* 262:750–754; Northrop et al. (1994) *Nature* 369:497–502; Masuda et al. (1995) *Mol. Cell. Biol.* 15:2697–2706; Hoey et al. (1995) *Immunity* 2:461–472; Ho et al. (1995) *J. Biol. Chem.* 270:19898–19907). In resting T cells NFAT proteins are present in the cytoplasm as phosphorylated species. Upon activation, sustained increases in calcium activate the phosphatase, calcineurin, which subsequently dephosphorylates NFAT (Beals, C. R., et al. 1997. Genes Dev. 11, 824–834.; Clipstone, N. A. and Crabtree, G. R. 1992. Nature 357, 695–697.; Flanagan, W. M., et al. 1991. Nature 352, 803–807) which is then quickly translocated into the nucleus to drive gene expression in association with other factors such as c-Maf, AP-1 and NIP45 (Cockerill, P. N., et al. 1993. Proc. Natl. Acad. Sci. USA 90, 2466–2470.; Rooney, J. W., et al. 1995. Immunity 2, 545–553.; Ho, I-C., et al. 1996. Cell 85, 973–983.; Hodge, M. R., et al. 1996; Beals, C. R., et al. 1997. Science 275, 1930–1933). The activation-dependent dephosphorylation and translocation of NFAT in lymphocytes and in cardiac endothelial and muscle cells can be blocked by immunosuppressive drugs such as cyclosporin A (CsA) or tacrolimus (FK506) which block calcineurin (Emmel, E. A., et al. 1989. Science 246, 1617–1620).

The cytoplasmic subunit of NFAT is encoded by a family of genes including NFATp, NFATc, NFAT3, and NFAT4/x, all of which bind to and transactivate NFAT target sequences in vitro (see e.g., Hoey et al. (1995) *Immunity* 2:461–472; Masuda et al. (1995) *Mol. Cell. Biol.* 15:2697–2706; McCaffrey et al. (1993) *Science* 262:750–754; Northrop et al. (1994) *Nature* 369:497–502). These family members share approximately 70% sequence identity within a region related to the Rel homology domain. The first member of the family to be purified and cloned was NFATp (see e.g., McCaffrey et al. (1993) *Science* 262:750–754). NFATp (also referred to as NFAT1) is constitutively expressed as a cytoplasmic phosphoprotein in resting immune cells (see e.g., Shaw et al. (1995) *Proc. Natl. Acad. Sci.* 92:11205–11209). Upon stimulation of the immune cells, NFATp is dephosphorylated by a calcium-calcineurin dependent pathway and translocates to the nucleus. Following translocation to the nucleus, nuclear NFAT associates with a nuclear component econtaining fos and jun proteins (see e.g., Rao (1994) *Immunology Today.* 15:274–281), which are synthesized by stimuli that activate protein kinase C. The associated NFAT complex binds to the IL-2 promoter to initiate expression of the IL-2 gene.

Despite their name, NFAT proteins are not only expressed in T cells, but also in other classes of immune-system cells. NFAT proteins are activated by stimulation of receptors coupled to calcium mobilization, such as the antigen receptors on T and B cells, the Fcε receptors on mast cells and basophils, the Fcγ receptors on macrophages and NK cells, and receptors coupled to certain heterotrimeric G proteins (see e.g., Rao (1994) *Immunology Today.* 15:274–281; Venkataraman et al. (1994) *Immunity* 1:189–196; Choi et al. (1994) *Immunity* 1:179–187; Weiss et al. (1996) *Mol. Cell. Biol.* 16:228–235; Aramburu et al. (1995) *J. Exp. Med.* 182:801–810).

Proteins belonging to the NFAT family also play a central role in other inducible gene transcription during the immune response (see e.g., Rao (1994) *Immunology Today.* 15:274–281; Crabtree et al. (1994) *Annu. Rev. Biochem.* 63:1045–1083). The involvement of NFAT is well established for the IL-2, IL-4, GM-CSF, and TNF-α cytokine genes in T cells. There is good but less extensive evidence for NFAT regulation of the IL-3, IL-5, IL-8, interferon-γ (IFN-γ) and CD40L genes in T cells, the TNF-α gene in B cells, and the IL-4 and IL-5 genes in mast cells. Cooperative binding of NFAT has also been noted in the promoter regions of the IL-2, IL-4, IL-5, and CD40L genes, and in the GM-CSF enhancer.

Although NFATp MRNA has been detected in brain, heart, and skeletal muscle, NFATp protein expression has not been detected in bulk extracts of these tissues (see e.g., Wang et al. (1995) *Annu. N.Y. Acad. Sci.* 766:182–194). Consistent findings are that NFATp and NFATc mRNAs are expressed in peripheral lymphoid tissue (spleen, PBL), and that NFAT4/x MRNA is expressed at high levels in the thymus, suggesting a role in T cell development. NFAT3 mRNA is expressed at low levels in lymphoid tissues (see e.g., Hoey et al. (1995) *Immunity* 2:461–472), and thus this protein may be preferentially expressed outside the immune system.

The function of NFATp in the immune response has been explored by targeted disruption of the NFATp gene (see e.g., Hodge et al. (1996) *Immunity* 4:397–405; Xanthoudakis et al. (1996) *Science* 272:892–895). In both cases the targeted exon was in the DNA-binding domain, and its disruption resulted either in the expression of a deleted version of the protein without DNA-binding activity (see e.g., Hodge et al. (1996) *Immunity* 4:397–405), or in no protein expression (see e.g., Xanthoudakis et al. (1996) *Science* 272:892–895). Mice deficient in the NFAT gene developed normally, however, displayed splenomegaly with hyperproliferation of both B and T cells. They also displayed early defects in the transcription of multiple genes encoding cytokines and cell surface receptors, and a striking defect in in vivo IL-4 production. Despite this early defect in IL-4 production, certain immune responses were enhanced at later time points, particularly the development of Th2 cells, evidenced by increased IL-4 production and IgE levels (see e.g., Hodge et al. (1996) *Immunity* 4:397–405).

SUMMARY OF THE INVENTION

This invention pertains to methods and compositions relating to modulation of cartilage cell growth and/or differentiation by modulation of NFATp activity. It has now been discovered that NFATp plays a critical role in regulating the growth and/or differentiation of cartilage. The invention is based, at least in part, on the observation that mice lacking NFATp, as they age, develop tumors that arise from articular cartilage and from the surrounding extraarticular connective tissue. Cartilage cell lines established from these tumors were aneuploid and displayed loss of contact inhibition. These data demonstrate that NFATp represses cartilage cell division, extinguishes the cartilage phenotype and displays the properties of a tumor suppressor gene. To our knowledge this is the first demonstration of a role for NFATp in regulating cartilage cell growth and differentiation and the first example of a regulatory factor that affects the growth of cartilage cells in the upper proliferative zone of articular cartilage and cartilage cell differentiation at the level of the adult mesenchymal progenitor cell. Furthermore, the absence of NFATp results in induction of chondrogenesis in extraarticular connective tissue.

Accordingly, the invention provides methods for identifying compounds that modulate cartilage growth and/or differentiation, methods for modulating cartilage cell growth and/or differentiation using agents that modulate NFATp activity (e.g., methods to expand cartilage cells in culture by inhibiting NFATp activity in the cells such that proliferation of the cartilage cells is stimulated) and methods for diagnosing disorders associated with aberrant cartilage growth and/or differentiation (e.g., chondrosarcomas) based on assessing a change in the expression of NFATp (e.g., the level of expression or the form of NFATp expressed).

In one aspect, the invention pertains to methods of identifying a compound that modulates cartilage growth and/or differentiation by contacting cartilage cells deficient in NFATp with a test compound and determining the effect of the test compound on the growth and/or differentiation of the cartilage cells. The test compound is identified as a modulator of cartilage growth and/or differentiation based on the ability of the test compound to modulate the growth and/or differentiation of the cartilage cells deficient in NFATp. Cartilage cells deficient in NFATp can be contacted with a test compound in vivo in a non-human NFATp deficient animal, for example, a mouse, by administering the test compound to the non-human NFATp deficient animal. Cartilage cells deficient in NFATp may also be isolated from a non-human NFATp deficient animal and contacted with the test compound ex vivo by culturing the test compound with the isolated cartilage cells.

In another aspect, the invention pertains to a method of identifying a compound that modulates cartilage growth and/or differentiation using an indicator composition comprising NFATp protein, wherein a test compound that modulates the activity of NFATp is selected and then the effect of this selected compound on cartilage growth and/or differentiation is assessed. In the method, the indicator composition comprising NFATp first is contacted with each member of a library of test compounds. The test compound(s) that modulate the activity of NFATp protein are selected and the ability of the selected compound to modulate cartilage growth and/or differentiation is determined. The indicator composition can be, for example, a cell that expresses NFATp protein, a cell that has been engineered to express the NFATp protein by introducing an expression vector encoding the NFATp protein into the cell or a cell free composition. Alternatively, the indicator composition may be a cell or cell-free composition that includes an NFATp protein and a target molecule, and the ability of the test compound to modulate the interaction of the NFATp protein with a target molecule is monitored. In another embodiment, the indicator composition is an indicator cell which comprises an NFATp protein and a reporter gene responsive to the NFATp protein. The level of expression of the reporter gene can be used to determine the ability of a test compound to modulate the activity of NFATp protein by producing an indicator cell that contains a recombinant expression vector encoding the NFATp protein and a vector comprising an NFATp-responsive regulatory element operatively linked a reporter gene. The indicator cell is contacted with a test compound and the level of expression of the reporter gene in the indicator cell in the presence of the test compound is determined. By comparing the level of expression of the reporter gene in the indicator cell in the presence of the test compound with the level of expression of the reporter gene in the indicator cell in the absence of the test compound, a compound of interest that modulates the activity of NFATp protein can be determined.

In another aspect, the invention pertains to a method for modulating cartilage cell growth and/or differentiation by contacting cartilage cells with a modulator of NFATp activity such that the growth and/or differentiation of the cartilage cells is modulated. In one aspect, this modulatory method pertains to methods of expanding cartilage cells in vitro, through culture of the cells with an inhibitor of NFATp activity such that proliferation of the cartilage cells is stimulated. In another aspect, this modulatory method pertains to methods of modulating aberrant cartilage growth and/or differentiation in a subject by administering to the subject a therapeutically effective amount of a specific modulator of NFATp activity such that aberrant cartilage growth and/or differentiation in a subject is modulated. In one embodiment, the modulator inhibits NFATp activity, for example, an antisense oligonucleotide, an intracellular antibody or a peptide that inhibits the interaction of NFATp with calcineurin. In another embodiment, the modulator stimulates NFATp activity, for example, an expression vector encoding NFATp. The modulator can be administered directly to an articulation site of a subject, or can be contacted ex vivo with cartilage cells isolated from a subject, followed by administration of the cartilage cells back into the subject.

In another aspect, the invention pertains to a method of diagnosing a subject for a disorder associated with aberrant cartilage growth and/or differentiation by detecting a change in expression of NFATp in cartilage cells of a subject suspected of having a disorder associated with aberrant cartilage growth and/or differentiation. The expression of NFATp in cartilage cells of a subject suspected of having the disorder is compared to the expression of NFATp in cartilage cells of a control subject without the disorder. The diagnosis for a disorder in a subject is based on a change in expression of NFATp (e.g., the level or form of NFATp) in cartilage cells relative to a control subject. For example, elevated levels of NFATp expression or expression of a constitutively active mutant form of NFATp may be associated with a disorder characterized by deficient cartilage growth and/or differentiation, while reduced levels of NFATp expression or expression of an inactive mutant form of NFATp may be associated with a disorder characterized by increased cartilage cell growth and/or differentiation, e.g., chondrosarcomas.

Kits for performing the various methods of the invention are also encompassed by the invention.

DETAILED DESCRIPTION OF THE INVENTION

Figure 1:
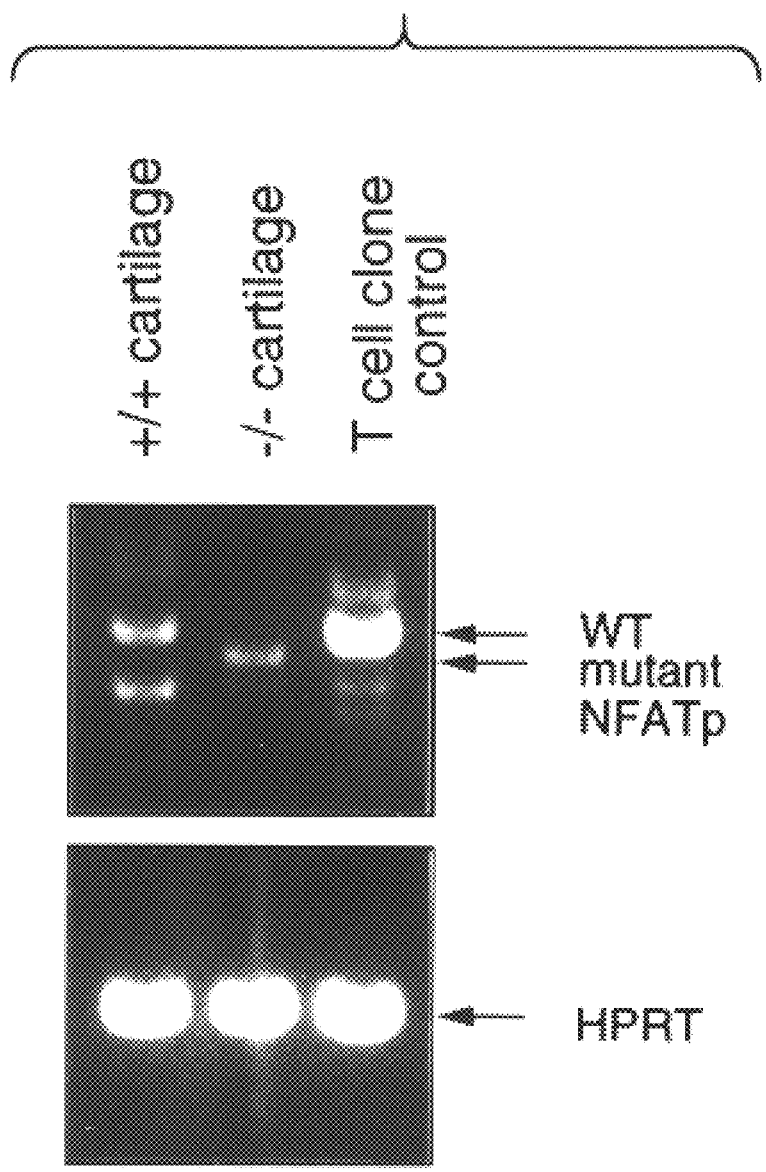
FIG. 1 is a reverse transcriptase-polymerase chain reaction (RT-PCR) analysis of NFATp mRNA from wild type and NFATp−/− cartilage cells.

This invention pertains to methods and compositions relating to modulation of cartilage growth and/or differentiation by modulation of NFATp activity. The invention is based, at least in part, on the surprising discovery that mice deficient in the NFATp protein exhibit increased articular cartilage growth and differentiation and have a high incidence of cartilage tumors that display characteristics of chondrosarcomas. The data described herein demonstrate that NFATp represses cartilage cell division and displays the properties of a tumor suppressor gene. These results are unexpected since NFAT proteins in general and NFATp in particular have not previously been implicated in regulating cartilage growth and/or differentiation.

In one aspect, the invention pertains to a method of identifying a compound that modulates cartilage growth and/or differentiation. In one embodiment of these screening assays, cartilage cells deficient in NFATp are contacted with a test compound to identify compounds that modulate cartilage growth and/or differentiation. In another embodiment of these screening assays, an indicator composition that includes NFATp is used to identify and select compounds that modulate NFATp activity and then the effect of the selected compounds on cartilage growth and/or differentiation is evaluated.

In another aspect, the invention pertains to method for modulating growth and/or differentiation of cartilage cells, either in vitro or in vivo, using modulators of NFATp activity. In one embodiment, cartilage cells (e.g., cartilage cells isolated from a subject) are contacted with a modulator compound by culturing the cartilage cells with the modulator in vitro. The cartilage cells, or mature cartilage that has formed upon proliferation and differentiation of the cartilage cells on culture, can then be readministered to the subject. In another embodiment, aberrant cartilage growth and/or differentiation in a subject is modulated by administering to the subject a therapeutically effective amount of a modulator of NFATp activity such that aberrant cartilage growth and/or differentiation in a subject is modulated. Use of modulators that inhibit or stimulate NFATp activity are encompassed by these modulatory methods of the invention.

In yet another aspect, the invention pertains to a method of diagnosing a subject for a disorder associated with aberrant cartilage growth and/or differentiation by detecting a change in expression of NFATp in cartilage cells of a subject suspected of having a disorder associated with aberrant cartilage growth and/or differentiation.

So that the invention may be more readily understood, certain terms are first defined.

As used herein, the term "NFATp" is intended to refer to a protein, also known in the art as NFAT1, that is a DNA binding protein, expressed in T cells, and has an amino acid sequence as described in, for example, U.S. Pat. No. 5,656,452 by Rao et al., U.S. Pat. No. 5,612,455 by Hoey, or other mammalian homologs thereof.

As used herein, the various forms of the term "modulate" are intended to include stimulation (e.g., increasing or upregulating a particular response or activity) and inhibition (e.g., decreasing or downregulating a particular response or activity).

As used herein, the term "cartilage cell" includes differentiated cartilage cells, (e.g., chondroblasts or atricular cartilage cells) as well as undifferentiated mesenchymal stem cells which can be induced to differentiate alone a chondrogenic pathway, e.g., to form chondroblasts. Preferably, a "cartilage cell" as defined herein expresses or can be induced to express Type II collagen.

As used herein, the term modulation of "growth and/or differentiation" includes the modulation of proliferation of a differentiated cartilage cell, the modulation of the state of differentiation of differentiated cartilage cells, as well as or in addition to the induction of a pathway in a mesenchymal stem cell which directs the stem cell to differentaite along a chondrogenic pathway, i.e., leading to the expression of a cartilage cell phenotype. In addition, the term "growth and/or differentiation" of a cartilage cell also includes the process of endochondral ossification which leads to the calcification of cartilage. In this process, the central portion of a cartilaginous matrix is resorbed to form the marrow cavity (cavitation). The more superficial cartilage cells at the ends of the long bones further differentiate and synthesize the matrix components of the surface and superficial layers of the true articular cartilage. A second group of cartilage cells distally also proliferates and undergoes a progressive differentiation and synthesis of a cartilage matrix which calcifies and is ultimately resorbed and replaced by osteoblasts to form bone. (see, e.g., Mankin, H. J. (1962) *J. Bone Joint Surg.* 44-A: 682–688; Mankin, H. J. (1963) *J. Bone Joint Surg.* 45-A, 529–540). Accordingly, the methods of modulating the growth and/or differentiation of cartilage cells described herein can also be used to modulate endochondral ossification and, thus, can be used in the repair of bone, e.g., to repair fractures.

As used herein, the term "contacting" (i.e., contacting a cell e.g. a cartilage cell, with an compound) is intended to include incubating the compound and the cell together in vitro (e.g., adding the compound to cells in culture) and administering the compound to a subject such that the compound and cells of the subject are contacted in vivo. The term "contacting" is not intended to include exposure of cartilage cells to an NFATp modulator that may occur naturally in a subject (i.e., exposure that may occur as a result of a natural physiological process).

As used herein, the term "test compound" is intended to refer to a compound that has not previously been identified as, or recognized to be, a modulator of NFATp activity and/or of cartilage cell growth and/or differentiation.

The term "library of test compounds" is intended to refer to a panel comprising a multiplicity of test compounds.

As used herein, the term "cartilage cells deficient in NFATp" is intended to include cells of a subject that are naturally deficient in NFATp, as wells as cells of a non-human NFATp deficient animal, e.g., a mouse, that have been altered such that they are deficient in NFATp. The term "cartilage cells deficient in NFATp" is also intended to include cartilage cells isolated from a non-human NFATp deficient animal or a subject that are cultured in vitro.

As used herein, the term "non-human NFATp deficient animal" refers to a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal, such that the endogenous NFATp gene is altered, thereby leading to either no production of NFATp or production of a mutant form of NFATp having deficient NFATp activity. Preferably, the activity of NFATp is entirely blocked, although partial inhibition of NFATp activity in the animal is also encompassed.

As used herein, the term "indicator composition" refers to a composition that includes NFATp protein, for example, a cell that naturally expresses NFATp protein, a cell that has been engineered to express the NFATp protein by introducing an expression vector encoding the NFATp protein into the cell, or a cell free composition that contains NFATp (e.g., naturally-occurring NFATp or recombinantly-engineered NFATp).

As used herein, the term "engineered" (as in an engineered cell) refers to a cell into which an expression vector encoding the NFATp protein has been introduced.

As used herein, the term "cell free composition" refers to an isolated composition which does not contain intact cells. Examples of cell free compositions include cell extracts and compositions containing isolated proteins.

As used herein, the term "a target molecule" for NFATp refers a molecule with which NFATp can interact, including other proteins and DNA sequences, including for example, the IL-2, IL-4, GM-CSF, TNF-α, IL-3, and IL-4 promoter/enhancer regions, AP-1 protein and I☐B protein.

As used herein, the term "reporter gene responsive to NFATp" refers to any gene that expresses a detectable gene product, which may be RNA or protein. Preferred reporter genes are those that are readily detectable. The reporter gene may also be included in a construct in the form of a fusion gene with a gene that includes desired transcriptional regulatory sequences or exhibits other desirable properties. Examples of reporter genes include, but are not limited to CAT (chloramphenicol acetyl transferase) (Alton and Vapnek (1979), Nature 282: 864–869) luciferase, and other enzyme detection systems, such as beta-galactosidase; firefly luciferase (deWet et al. (1987), Mol. Cell. Biol. 7:725–737); bacterial luciferase (Engebrecht and Silverman (1984), PNAS 1: 4154–4158; Baldwin et al. (1984), Biochemistry 23: 3663–3667); alkaline phosphatase (Toh et al. (1989) Eur. J. Biochem. 182: 231–238, Hall et al. (1983) J. Mol. Appl. Gen. 2: 101), human placental secreted alkaline phosphatase (Cullen and Malim (1992) Methods in Enzymol. 216:362–368) and green fluorescent protein (U.S. Pat. No. 5,491,084; WO 96/23898).

As used herein, the term "NFATp-responsive element" refers to a DNA sequence that is directly or indirectly regulated by the activity of the NFATp (whereby activity of NFATp can be monitored, for example, via transcription of the reporter genes).

As used herein, the term "aberrant" (as in aberrant cartilage growth and/or differentiation) refers to cartilage growth and/or differentiation that deviates from normal cartilage growth and/or differentiation in a subject. The aberrant growth and/or differentiation can either be excessive cartilage growth and/or differentiation or reduced cartilage growth and/or differentiation with respect to normal cartilage growth and/or differentiation in a subject.

As used herein, the term "a modulator of NFATp activity" is intended to refer to an agent, for example a compound or compounds, which modulates transcription of an NFATp gene, translation of NFATp MRNA or activity of an NFATp protein. A "modulator of NFATp activity" also includes compounds that indirectly modulate NFATp activity, for example, modulators of a signal transduction pathway that may include NFATp, such as inhibitors of calcineurin which prevent calcineurin from dephosphorylating NFATp and the subsequent translocation of NFATp to the nucleus. In one embodiment, for the treatment of arthritis (e.g., rheumatoid arthritis) the modulator is not cyclosporin A, FK506 or other immunophilin-binding agent. Examples of modulators that directly modulate NFATp activity include antisense nucleic acid molecules that bind to NFATp mRNA or genomic DNA, intracellular antibodies that bind to NFATp intracellularly and modulate (i. e., inhibit) NFATp activity, NFATp peptides that inhibit the interaction of NFATp with a target molecule (e.g, calcineurin) and expression vectors encoding NFATp that allow for increased expression of NFATp activity in a cell, as well as chemical compounds that act to specifically modulate the activity of NFATp.

As used herein, an "antisense oligonucleotide" refers to a nucleic acid that comprises a nucleotide sequence which is complementary to a "sense" nucleic acid encoding a protein, e.g., complementary to the coding strand of a double-stranded cDNA molecule, complementary to an MRNA sequence or complementary to the coding strand of a gene. Accordingly, an antisense nucleic acid can hydrogen bond to a sense nucleic acid.

As used herein, the term "intracellular antibody" is intended to include immunoglobulin molecules and immunologically active portions of immunoglobulin molecules, i.e., molecules that contain an antigen binding site which specifically binds (immunoreacts with) an antigen, such as Fab and F(ab')$_2$ fragments. The term "intracellular antibody" is also intended to refer to an antibody that functions in an intracellular region of a cell, e.g., the cytoplasm or nucleus, to modulate the expression or activity of the NFATp.

As used herein, the term "articulation site" is used interchangeably with "joint" and refers to the region where various bones of the skeleton are connected. In particular, the term "articulation site" refers to movable joints which are covered by cartilage that is held together by ligaments and is partially lined with synovial membrane which secretes fluid to lubricate the joint. The cartilage which covers the articular surface of the bone is referred to as articular cartilage.

As used herein, the term "diagnosing" refers to identifying a disorder in a subject or the susceptibility of a subject to the disorder (e.g., a predisposition to develop a disorder). Various aspects of the present invention are described in further detail in the following subsections.

I. Screening Assays to Identify Compounds that Modulate Cartilage Growth and/or Differentiation A. Assays Using NFATp Deficient Cells In one embodiment, the invention provides methods for identifying compounds that modulate cartilage growth and/ or differentiation using cells deficient in NFATp. As described in the Examples, inhibition of NFATp activity (e.g., by disruption of the NFATp gene) leads to cartilage cells with increased proliferative capacity. Accordingly, these highly proliferative cartilage cells deficient in NFATp can be used to identify agents that modulate cartilage growth and/or differentiation by means other than modulating NFATp itself.

In the screening method, cartilage cells deficient in NFATp are contacted with a test compound and the growth and/or differentiation of the cartilage cells is monitored. Modulation of growth and/or differentiation of the NFATp deficient cartilage cells (as compared to an appropriate control such as, for example, untreated cells or cells treated with a control agent) identifies a test compound as a modulator of cartilage growth and/or differentiation. In one embodiment, the test compound is administered directly to a non-human NFATp deficient animal, preferably a mouse, to identify a test compound that modulates the in vivo growth and/or differentiation of cartilage cells deficient in NFATp. In another embodiment, cartilage cells deficient in NFATp are isolated from the non-human NFATp deficient animal, and contacted with the test compound ex vivo to identify a test compound that modulates growth and/or differentiation of the isolated cartilage cells deficient in NFATp. In preferred embodiments, growth and/or differentiation of the cartilage cells deficient in NFATp is inhibited by the test compound.

Cells deficient in NFAT can be obtained from a non-human animals created to be deficient in NFATp. Preferred non-human animals include monkeys, dogs, cats, mice, rats, cows, horses, goats and sheep. In preferred embodiments, the NFATp deficient animal is a mouse. Mice deficient in NFATp have been described in the art (see Hodge et al. (1996) *Immunity* 4:397–405; Xanthoudakis et al. (1996) *Science* 272:892–895). Non-human NFATp deficient animals typically are created by homologous recombination. Briefly, a vector is prepared which contains at least a portion of the NFATp gene into which a deletion, addition or substitution has been introduced to thereby alter, e.g., functionally disrupt, the endogenous NFATp gene. The NFATp gene preferably is a mouse NFATp gene. For example, a mouse NFATp gene can be isolated from a mouse genomic DNA library using the mouse NFATp cDNA as a probe. The mouse NFATp gene then can be used to construct a homologous recombination vector suitable for altering an endogenous NFATp gene in the mouse genome. In a preferred embodiment, the vector is designed such that, upon homologous recombination, the endogenous NFATp gene is functionally disrupted (i.e., no longer encodes a functional protein; also referred to as a "knock out" vector). Alternatively, the vector can be designed such that, upon homologous recombination, the endogenous NFATp gene is mutated or otherwise altered but still encodes functional protein (e.g., the upstream regulatory region can be altered to thereby alter the expression of the endogenous NFATp protein). In the homologous recombination vector, the altered portion of the NFATp gene is flanked at its 5' and 3' ends by additional nucleic acid of the NFATp gene to allow for homologous recombination to occur between the exogenous NFATp gene carried by the vector and an endogenous NFATp gene in an embryonic stem cell. The additional flanking NFATp nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced NFATp gene has homologously recombined with the endogenous NFATp gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by gernline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Bems et al.

NFATp deficient mice created by homologous recombination having a disrupted NFATp gene can be generated, for example, as described by Hodge et al. (1996) *Immunity* 4:397–405, the contents of which are expressly incorporated herein by reference. The targeted exon was in the DNA-binding domain, and its disruption results in the expression of a deleted version of the protein without DNA-binding activity. These mice displayed significantly increased articular cartilage growth and/or differentiation which resulted in tumors, extensive extra articular calcification of cartilage cells and various degrees of joint destruction (see Example 1).

In one embodiment of the screening assay, compounds tested for their ability to modulate cartilage cell growth and/or differentiation are contacted with NFATp deficient cartilage cells by administering the test compound to a non-human NFATp deficient animal in vivo and evaluating the effect of the test compound on cartilage growth and/or differentiation in the animal. The test compound can be administered to a non-human NFATp deficient animal as a pharmaceutical composition. Such compositions typically comprise the test compound and a pharmaceutically acceptable carrier. As used herein the term "pharmaceutically acceptable carrier" is intended to include any and all solvents, dispersion media, coatings, antibacterial and antifungal compounds, isotonic and absorption delaying compounds, and the like, compatible with pharmaceutical administration. The use of such media and compounds for pharmaceutically active substances is well known in the art. Except insofar as any conventional media or compound is incompatible with the active compound, use thereof in the compositions is contemplated. Supplementary active compounds can also be incorporated into the compositions.

A pharmaceutical composition of the invention is formulated to be compatible with its intended route of administration. For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid; buffers such as acetates, citrates or phosphates and compounds for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid.polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal compounds, for example, parabens, chlorobutanol, phenol, ascorbic acid, thimerosal, and the like. In many cases, it will be preferable to include isotonic compounds, for example, sugars, polyalcohols such as manitol, sorbitol, sodium chloride in the composition. Prolonged absorption of the injectable compositions can be brought about by including in the composition an compound which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or be compressed into tablets. For the purpose of oral therapeutic administration, the active compound can be combined with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

In one embodiment, the test compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

In another embodiment, compounds that modulate cartilage cell growth and/or differentiation are identified by contacting the cartilage cells deficient in NFATp ex vivo with one or more test compounds, and determining the effect of the test compound on cartilage growth and/or differentiation. In one embodiment, NFATp deficient cartilage cells contacted with a test compound ex vivo may be readministered to a subject (e.g., an NFATp deficient subject).

For practicing the screening method ex vivo, cartilage cells deficient in NFATp can be isolated from a non-human NFATp deficient animal by standard methods and incubated (i e., cultured) in vitro with a test compound. Methods for isolating and culturing cartilage cells from NFATp deficient mice are described in detail in Example 2. Moreover, methods for isolating cartilage cells are known in that art (see e.g., Brittberg et al., (1996) *Clinical Orthopaedics and Related Research* 326; 270–283; Vacanti et al., (1994) *Amer. J. Sports Med.* 22; 485–488; Derfus et al., (1996) *Connective Tissue Res.* 35; 337–342; Kim et al., (1993) *Plastic and Reconstructive Surgery.* 94; 580–584; Kandel et al., (1995) *Art Cells Blood Subs and Immob Biotech.* 23; 565–577).

Following contact of the NFATp deficient cartilage cells with a test compound (either ex vivo or in vivo), the effect of the test compound on the growth and/or differentiation of the cartilage cells can be determined by any one of a variety of suitable methods, including light microscopic analysis of the cartilage cells, histochemical analysis of the cartilage cells or analysis of the proliferative capacity of the cartilage cells. Examples of each of these methods are described in detail in the Examples. A test compound is identified as a modulator of cartilage growth and/or differentiation based on its ability to modulate the growth and/or differentiation of NFATp deficient cartilage cells, as compared to an appropriate control (such as untreated cells or cells treated with a control compound, or carrier, that does not modulate cartilage growth and/or differentiation).

B. Assay Using NFATp-Containing Indicator Compositions

In another embodiment, the invention provides methods for identifying compounds that modulate cartilage growth and/or differentiation using indicator compositions that include NFATp. As described in the Examples, NFATp has been demonstrated to be a regulator of cartilage cell growth and differentiation. Accordingly, compounds that specifically modulate the activity of NFATp can be identified, as described herein, and the effect of a selected test compound on cartilage growth and/or differentiation can be evaluated.

Thus, another aspect of the invention pertains to screening assays for identifying compounds that modulate cartilage growth and/or differentiation comprising, providing an indicator composition comprising NFATp protein;

contacting the indicator composition with each member of a library of test compounds;

selecting from the library of test compounds a compound of interest that modulates the activity of NFATp protein; and determining the effect of the compound of interest on cartilage growth and/or differentiation to thereby identify a compound that modulates cartilage growth and/or differentiation.

The indicator composition can be a cell that expresses NFATp protein, for example, a cell that naturally expressed NFATp (e.g., a T cell) or, more preferably, a cell that has been engineered to express the NFATp protein by introducing into the cell an expression vector encoding the NFATp protein. Alternatively, the indicator composition can be a cell-free composition that includes NFATp (e.g. a cell extract from an NFATp-expressing cell or a composition that includes purified NFATp protein, either natural NFATp or recombinant NFATp). In one embodiment, the indicator composition includes an NFATp and a target molecule with which NFATp interacts, and the ability of the test compound to modulate the interaction of the NFATp protein with a target molecule is monitored to thereby identify the test compound as a modulator of NFATp activity.

In preferred embodiments, the indicator composition comprises an indicator cell, wherein the indicator cell comprises an NFATp protein and a reporter gene responsive to the NFATp protein. Preferably, the indicator cell contains:

a recombinant expression vector encoding the NFATp protein; and a vector comprising an NFATp-responsive regulatory element operatively linked a reporter gene; and the screening method comprises:

a) contacting the indicator cell with a test compound;

b) determining the level of expression of the reporter gene in the indicator cell in the presence of the test compound; and c) comparing the level of expression of the reporter gene in the indicator cell in the presence of the test compound with the level of expression of the reporter gene in the indicator cell in the absence of the test compound to thereby select a compound of interest that modulates the activity of NFATp protein.

Once a test compound is identified as modulating the activity of NFATp, the effect of the test compound on cartilage growth and/or differentiation is then tested.

NFATp-responsive elements that can be used in the reporter gene construct are known in the art and include, for example, upstream regulatory regions from cytokine genes such as the IL-2, IL-4, GM-CSF, and TNF-$\alpha$ genes. Examples of NFATp-responsive reporter gene constructs are described, for example, in PCT Publication WO 97/39721 by Glimcher et al.

A cell that has been engineered to express the NFATp protein can be produced by introducing into the cell an expression vector encoding the NFATp protein. Recombinant expression vectors that can be used for expression of NFATp protein in the indicator cell are known in the art. Typically the NFAT cDNA is first introduced into a recombinant expression vector using standard molecular biology techniques. An NFAT cDNA can be obtained, for example, by amplification using the polymerase chain reaction (PCR) or by screening an appropriate cDNA library. The nucleotide sequences of NFATp cDNAs (e.g., mouse and human) are known in the art and can be used for the design of PCR primers that allow for amplification of a cDNA by standard PCR methods or for the design of a hybridization probe that can be used to screen a cDNA library using standard hybridization methods. The nucleotide and predicted amino acid sequences of a mammalian NFATp cDNA are disclosed in McCaffrey, P. G. et al. (1993) *Science* 262:750–754 (see also U.S. Pat. No. 5,656,452 by Rao and U.S. Pat. No. 5,612,455 by Hoey).

Following isolation or amplification of a NFATp cDNA, the DNA fragment is introduced into an expression vector. As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid in a form suitable for expression of the nucleic acid in a host cell, which means that the recombinant expression vectors include one or more regulatory sequences, selected on the basis of the host cells to be used for expression and the level of expression desired, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell, those which direct expression of the nucleotide sequence only in certain host cells (e.g., tissue-specific regulatory sequences) or those which direct expression of the nucleotide sequence only under certain conditions (e.g., inducible regulatory sequences).

It will be appreciated by those skilled in the art that the design of the expression vector may depend on such factors as the choice of the host cell to be transformed, the level of expression of protein desired, etc. When used in mammalian cells, the expression vector's control functions are often provided by viral regulatory elements. For example, commonly used promoters are derived from polyoma virus, adenovirus, cytomegalovirus and Simian Virus 40. Nonlimiting examples of mammalian expression vectors include pCDM8 (Seed, B., (1987) *Nature* 329:840) and pMT2PC (Kaufman et al. (1987), *EMBO J.* 6:187–195). A variety of mammalian expression vectors carrying different regulatory sequences are commercially available. For constitutive expression of the nucleic acid in a mammalian host cell, a preferred regulatory element is the cytomegalovirus promoter/enhancer. Moreover, inducible regulatory systems for use in mammalian cells are known in the art, for example systems in which gene expression is regulated by heavy metal ions (see e.g., Mayo et al. (1982) *Cell* 29:99–108; Brinster et al. (1982) *Nature* 296:39–42; Searle et al. (1985) *Mol. Cell. Biol.* 5:1480–1489), heat shock (see e.g., Nouer et al. (1991) in *Heat Shock Response*, e.d. Nouer, L., CRC, Boca Raton, Fla., pp167–220), hormones (see e.g., Lee et al. (1981) *Nature* 294:228–232; Hynes et al. (1981) *Proc. Natl. Acad. Sci. USA* 78:2038–2042; Klock et al. (1987) *Nature* 329:734–736; Israel & Kaufman (1989) *Nucl. Acids Res.* 17:2589–2604; and PCT Publication No. WO 93/23431), FK506-related molecules (see e.g., PCT Publication No. WO 94/18317) or tetracyclines (Gossen, M. and Bujard, H. (1992) *Proc. Natl. Acad. Sci. USA* 89:5547–5551; Gossen, M. et al. (1995) *Science* 268:1766–1769; PCT Publication No. WO 94/29442; and PCT Publication No. WO 96/01313). Still further, many tissue-specific regulatory sequences are known in the art, including the albumin promoter (liver-specific; Pinkert et al. (1987) *Genes Dev.* 1:268–277), lymphoid-specific promoters (Calame and Eaton (1988) *Adv. Immunol* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916) and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

Vector DNA can be introduced into mammalian cells via conventional transfection techniques. As used herein, the various forms of the term "transfection" are intended to refer to a variety of art-recognized techniques for introducing foreign nucleic acid (e.g., DNA) into mammalian host cells, including calcium phosphate co-precipitation, DEAE-dextran-mediated transfection, lipofection, or electroporation. Suitable methods for transfecting host cells can be found in Sambrook et al. (*Molecular Cloning: A Laboratory Manual,* 2nd Edition, Cold Spring Harbor Laboratory press (1989)), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker may be introduced into a host cell on a separate vector from that encoding a maf family protein or, more preferably, on the same vector. Cells stably transfected with the introduced nucleic acid can be identified by drug selection (e.g., cells that have incorporated the selectable marker gene will survive, while the other cells die).

In another embodiment, the indicator composition is a cell free composition. NFATp expressed by recombinant methods in a host cell can be isolated from the host cells, or cell culture medium using standard methods for protein purifying, for example, by ion-exchange chromatography, gel filtration chromatography, ultrafiltration, electrophoresis, and immunoaffinity purification with antibodies specific for NFATp to produce NFATp protein that can be used in a cell free composition. Alternatively, an extract of NFATp-expressing cells can be prepared for use as cell-free composition.

In one embodiment, compounds that specifically modulate NFATp activity are identified based on their ability to modulate the interaction of NFATp with a target molecule to which NFATp binds. The target molecule can be a protein, such as c-fos, c-jun, AP-1 or NIP45. Alternatively, the target can be a DNA sequence (i.e., an NFATp-responsive element). Suitable assays are known in the art that allow for the detection of protein-protein interactions (e.g., immunoprecipitations, two-hybrid assays and the like) or that allow for the detection of interactions between a DNA binding protein with a target DNA sequence (e.g., electrophoretic mobility shift assays, DNAse I footprinting assays and the like). By performing such assays in the presence and absence of test compounds, these assays can be used to identify compounds that modulate (e.g., inhibit or enhance) the interaction of NFATp with a target molecule.

In one embodiment, the amount of binding of NFATp to the target molecule in the presence of the test compound is greater than the amount of binding of NFATp to the target molecule in the absence of the test compound, in which case the test compound is identified as a compound that enhances binding of NFATp. In another embodiment, the amount of binding of NFATp to the target molecule in the presence of the test compound is less than the amount of binding of NFATp to the target molecule in the absence of the test compound, in which case the test compound is identified as a compound that inhibits binding of NFATp.

In the methods of the invention for identifying test compounds that modulate an interaction between NFATp protein and a target molecule, the full NFATp protein may be used in the method, or, alternatively, only portions of the NFATp protein may be used. For example, an isolated NFAT Rel Homology Domain (RHD) (or a larger subregion of NFATp that includes the RHD) can be used. The degree of interaction between NFATp proteins and the target molecule can be determined, for example, by labeling one of the proteins with a detectable substance (e.g., a radiolabel), isolating the non-labeled protein and quantitating the amount of detectable substance that has become associated with the non-labeled protein. The assay can be used to identify test compounds that either stimulate or inhibit the interaction between the NFATp protein and a target molecule. A test compound that stimulates the interaction between the NFATp protein and a target molecule is identified based upon its ability to increase the degree of interaction between the NFATp protein and a target molecule as compared to the degree of interaction in the absence of the test compound, whereas a test compound that inhibits the interaction between the NFATp protein and a target molecule is identified based upon its ability to decrease the degree of interaction between the NFATp protein and a target molecule as compared to the degree of interaction in the absence of the compound. Assay systems for identifying compounds that modulate SH2 domain-ligand interactions as described in U.S. Pat. No. 5,352,660 by Pawson, can be adapted to identify test compounds that modulate NFATp-target molecule interaction.

Recombinant expression vectors that can be used for expression of NFATp in the indicator cell are known in the art (see discussions above). In one embodiment, within the expression vector the NFATp-coding sequences are operatively linked to regulatory sequences that allow for constitutive expression of NFATp in the indicator cell (e.g., viral regulatory sequences, such as a cytomegalovirus promoter/enhancer, can be used). Use of a recombinant expression vector that allows for constitutive expression of NFATp in the indicator cell is preferred for identification of compounds that enhance or inhibit the activity of NFATp. In an alternative embodiment, within the expression vector the NFATp coding sequences are operatively linked to regulatory sequences of the endogenous NFATp gene (i.e., the promoter regulatory region derived from the endogenous gene). Use of a recombinant expression vector in which NFATp expression is controlled by the endogenous regulatory sequences is preferred for identification of compounds that enhance or inhibit the transcriptional expression of NFATp.

A variety of reporter genes are known in the art and are suitable for use in the screening assays of the invention. Examples of suitable reporter genes include those which encode chloramphenicol acetyltransferase, beta-galactosidase, alkaline phosphatase or luciferase. Standard methods for measuring the activity of these gene products are known in the art.

A variety of cell types are suitable for use as an indicator cell in the screening assay. Preferably a cell line is used which expresses low levels of NFATp, such as human Jurkat T cell leukemia, murine T cell hybridoma BYDP, or COS cells.

In one embodiment, the level of expression of the reporter gene in the indicator cell in the presence of the test compound is higher than the level of expression of the reporter gene in the indicator cell in the absence of the test compound and the test compound is identified as a compound that stimulates the expression or activity of NFATp. In another embodiment, the level of expression of the reporter gene in the indicator cell in the presence of the test compound is lower than the level of expression of the reporter gene in the indicator cell in the absence of the test compound and the test compound is identified as a compound that inhibits the expression or activity of NFATp.

Alternative to the use of a reporter gene construct, compounds that modulate the expression or activity of NFATp can be identified by using other "read-outs." For example, an indicator cell can be transfected with a NFATp expression vector, incubated in the presence and in the absence of a test compound, and IL-2 cytokine production can be assessed by detecting cytokine mRNA (e.g., IL-2 MRNA) in the indicator cell or cytokine secretion (i.e., IL-2 secretion) into the culture supernatant. Standard methods for detecting cytokine mRNA, such as reverse transcription-polymerase chain reaction (RT-PCR) are known in the art. Standard methods for detecting cytokine protein in culture supernatants, such as enzyme linked immunosorbent assays (ELISA) are also known in the art.

Once a test compound is identified that modulates NFATp activity, by one of the variety of methods described hereinbefore, the selected test compound (or "compound of interest") can then be further evaluated for its effect on cartilage growth and/or differentiation, for example by contacting the compound of interest with cartilage cells either in vivo (e.g., by administering the compound of interest to a subject) or ex vivo (e.g., by isolating cartilage cells and contacting the isolated cartilage cells with the compound of interest or, alternatively, by contacting the compound of interest with a cartilage cell line, such as a chondrosarcoma cell line) and determining the effect of the compound of interest on the growth and/or differentiation of the cartilage cells, as compared to an appropriate control (such as untreated cells or cells treated with a control compound, or carrier, that does not modulate cartilage growth and/or differentiation). The effect of the test compound on the growth and/or differentiation of the cartilage cells can be determined as described above in subsection A (e.g., by light microscopic analysis of the cartilage cells, histochemical analysis of the cartilage cells or analysis of the proliferative capacity of the cartilage cells).

A variety of test compounds can be evaluated using the screening assays described in subsections A and B above. In certain embodiments, the compounds to be tested can be derived from libraries (i.e., are members of a library of compounds). While the use of libraries of peptides is well established in the art, new techniques have been developed which have allowed the production of mixtures of other compounds, such as benzodiazepines (Bunin et al. (1992). *J. Am. Chem. Soc.* 114:10987; DeWitt et al. (1993). *Proc. Natl. Acad. Sci. USA* 90:6909) peptoids (Zuckermann. (1994). *J. Med Chem.* 37:2678) oligocarbamates (Cho et al. (1993). *Science.* 261:1303–), and hydantoins (DeWitt et al. supra). An approach for the synthesis of molecular libraries of small organic molecules with a diversity of 104–105 as been described (Carell et al. (1994). *Angew. Chem. Int. Ed. Engl.* 33:2059–; Carell et al. (1994) Angew. *Chem. Int. Ed. Engl.* 33:2061–).

The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145). Other exemplary methods for the synthesis of molecular libraries can be found in the art, for example in: Erb et al. (1994). *Proc. Natl. Acad. Sci. USA* 91:11422–; Horwell et al. (1996) *Immunopharmacology* 33:68–; and in Gallop et al. (1994); *J. Med Chem.* 37:1233–.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) Proc Natl Acad Sci USA 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); In still another embodiment, the combinatorial polypeptides are produced from a cDNA library.

Exemplary compounds which can be screened for activity include, but are not limited to, peptides, nucleic acids, carbohydrates, small organic molecules, and natural product extract libraries.

II. Methods for Modulating Cartilage Growth and/or Differentiation

In another aspect, the invention features a method for modulating growth and/or differentiation of cartilage cells by contacting cartilage cells with a modulator of NFATp activity such that growth and/or differentiation of the cartilage cells is modulated. The modulatory methods of the invention are of particular interest for use in expanding populations of cartilage cells in vitro for administration to a subject with insufficient cartilage. Normal mature articular cartilage cells typically divide rarely or not at all even when the cartilage is subject to direct trauma, e.g., incision or excision of the cartilage surface (see e.g., Mankin, H. J. & Boyle, C. I. (1967) *Proceedings of the Workshop on Cartilage Degradation and Repair;* Mankin, H. J. (1974) *N. Engl. J. Med.* 291:1285). In contrast, mature articular cartilage cells lacking NFATp activity undergo uncontrolled cell division and differentiation into articular cartilage (see the Examples). As demonstrated in the Examples, NFATp deficient mice exhibit increased articular cartilage growth. As further demonstrated in the examples, cartilage cells deficient in NFATp isolated from NFATp deficient mice continue to proliferate in vitro, even after attaining confluency. In addition, expression of NFATp controls expression of the cartilage phenotyp.

Accordingly the invention provides a means to stimulate proliferation and/or differentiation of cartilage cells in vitro such that mature articular cartilage can be obtained for transplantation into a subject in need of cartilage. The invention also allows for modulation of aberrant cartilage growth and/or differentiation in a subject in vivo, by administering to the subject a therapeutically effective amount of a modulator of NFATp activity such that aberrant cartilage growth and/or differentiation in a subject is modulated. The term "subject" is intended to include living organisms in which an immune response can be elicited. Preferred subjects are mammals. Examples of subjects include humans, monkeys, dogs, cats, mice, rats cows, horses, goats, and sheep. Modulation of NFATp activity, therefore, provides a means to regulate aberrant cartilage growth and/or differentiation in various disease states. In one embodiment, for stimulation of cartilage growth and/or differentiation, the modulator inhibits NFATp activity. In another embodiment, to inhibit cartilage growth and/or differentiation, the modulator stimulates NFATp activity.

Identification of compounds that modulate the growth and/or differentiation of cartilage cells by modulating NFATp expression allows for selective manipulation of cartilage cells in a variety of clinical situations using the modulatory methods of the invention. The stimulatory methods of the invention (i.e., methods that use a stimulatory agent) result in increased production of NFATp, which suppresses cartilage growth and/or differentiation. In contrast, the inhibitory methods of the invention (i.e., methods that use an inhibitory agent) inhibit the production of NFATp and promotes cartilage growth and/or differentiation, as demonstrated in the Examples. Thus, to treat a disorder wherein inhibition of cartilage growth and/or differentiation is beneficial, a stimulatory method of the invention is selected such that NFATp expression is promoted. Alternatively, to treat a disorder wherein stimulation of cartilage growth and/or differentiation is beneficial, an inhibitory method of the invention is selected such that NFATp expression is downregulated. Application of the modulatory methods of the invention to the treatment of a disorder may result in cure of the disorder, a decrease in the type or number of symptoms associated with the disorder, either in the long term or short term (i.e., amelioration of the condition) or simply a transient beneficial effect to the subject.

Numerous disorders associated with aberrant cartilage growth and/or differentiation have been identified and could benefit from modulation of NFATp in the individual suffering from the disorder. Application of the immunomodulatory methods of the invention to such disorders is described in further detail below.

A. Inhibitory Compounds

Since inhibition of NFATp activity is associated with increased cartilage growth and/or differentiation, to stimulate cartilage growth and/or differentiation cartilage cells are contacted with an agent that inhibits NFATp activity. Cartilage cells may be contacted with the agent in vitro and then the cells can be administered to a subject or, alternatively, the agent may be administered to the subject (e.g., directly to an articular site at which cartilage growth and/or differentiation is desired). The methods of the invention using NFATp inhibitory compounds can be used in the treatment of disorders in which cartilage growth and/or differentiation is diminished, blocked, inhibited, downregulated or the like. The degradation of cartilage is a common feature of joint disease, such as rheumatoid arthritis and osteoarthritis. For example, in rheumatoid arthritis, inflammatory responses lead to destruction of cartilage, while in osteoarthritis cartilage is degraded by wear and tear. Accordingly, preferred disorders for treatment using an inhibitory compound of the invention include arthritis, including rheumatoid arthritis and osteoarthritis, and other diseases associated with cartilage degradation (e.g., osteoporosis).

Inhibitory compounds of the invention can be, for example, intracellular binding molecules that act to specifically inhibit the expression or activity of NFATp. As used herein, the term "intracellular binding molecule" is intended to include molecules that act intracellularly to inhibit the expression or activity of a protein by binding to the protein or to a nucleic acid (e.g., an mRNA molecule) that encodes the protein. Examples of intracellular binding molecules, described in further detail below, include antisense nucleic acids, intracellular antibodies, peptidic compounds that inhibit the interaction of NFATp with a target molecule (e.g, calcineurin) and chemical agents that specifically inhibit NFATp activity.

i. Antisense Nucleic Acid Molecules

In one embodiment, an inhibitory compound of the invention is an antisense nucleic acid molecule that is complementary to a gene encoding NFATp, or to a portion of said gene, or a recombinant expression vector encoding said antisense nucleic acid molecule. The use of antisense nucleic acids to downregulate the expression of a particular protein in a cell is well known in the art (see e.g, Weintraub, H. et al, Antisense RNA as a molecular tool for genetic analysis, *Reviews—Trends in Genetics,* Vol. 1(1) 1986; Askari, F. K. and McDonnell, W. M. (1996) *N. Eng J. Med.* 334:316–318; Bennett, M. R. and Schwartz, S. M. (1995) *Circulation* 92:1981–1993; Mercola, D. and Cohen, J. S. (1995) *Cancer Gene Ther.* 2:47–59; Rossi, J. J. (1995) *Br. Med. Bull.* 51:217–225; Wagner, R. W. (1994) *Nature* 372:333–335). An antisense nucleic acid molecule comprises a nucleotide sequence that is complementary to the coding strand of another nucleic acid molecule (e.g., an mRNA sequence) and accordingly is capable of hydrogen bonding to the coding strand of the other nucleic acid molecule. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). Furthermore, an antisense nucleic acid can be complementary in sequence to a regulatory region of the gene encoding the mRNA, for instance a transcription initiation sequence or regulatory element. Preferably, an antisense nucleic acid is designed so as to be complementary to a region preceding or spanning the initiation codon on the coding strand or in the 3' untranslated region of an mRNA.

Given the known nucleotide sequence for the coding strand of the NFATp gene (and thus the known sequence of the NFATp mRNA), antisense nucleic acids of the invention can be designed according to the rules of Watson and Crick base pairing. The antisense nucleic acid molecule can be complementary to the entire coding region of a NFATp mRNA, but more preferably is an oligonucleotide which is antisense to only a portion of the coding or noncoding region of a NFATp mRNA. For example, the antisense oligonucleotide can be complementary to the region surrounding the translation start site of a NFATp mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. To inhibit NFATp expression in cells in culture, one or more antisense oligonucleotides can be added to cells in culture media.

Alternatively, an antisense nucleic acid can be produced biologically using an expression vector into which all or a portion of NFATp cDNA has been subcloned in an antisense orientation (i.e., nucleic acid transcribed from the inserted nucleic acid will be of an antisense orientation to a target nucleic acid of interest). Regulatory sequences operatively linked to a nucleic acid cloned in the antisense orientation can be chosen which direct the expression of the antisense RNA molecule in a cell of interest, for instance promoters and/or enhancers or other regulatory sequences can be chosen which direct constitutive, tissue specific or inducible expression of antisense RNA. The antisense expression vector is prepared according to standard recombinant DNA methods for constructing recombinant expression vectors, except that the NFATp cDNA (or portion thereof) is cloned into the vector in the antisense orientation. The antisense expression vector can be in the form of, for example, a recombinant plasmid, phagemid or attenuated virus. The antisense expression vector is introduced into cells using a standard transfection technique.

The antisense nucleic acid molecules of the invention are typically administered to a subject or generated in situ such that they hybridize with or bind to cellular mRNA and/or genomic DNA encoding a NFATp protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of an antisense nucleic acid molecule of the invention includes direct injection at a tissue site. Alternatively, an antisense nucleic acid molecule can be modified to target selected cells and then administered systemically. For example, for systemic administration, an antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an ($\alpha$-anomeric nucleic acid molecule. An ($\alpha$-anomeric nucleic acid molecule forms specific double-stranded hybrids with complementary RNA in which, contrary to the usual $\beta$-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave NFATp mRNA transcripts to thereby inhibit translation of NFATp mRNAs. A ribozyme having specificity for a NFATp-encoding nucleic acid can be designed based upon the nucleotide sequence of the NFATp cDNA. For example, a derivative of a Tetrahymena L-19 IVS RNA can be constructed in which the nucleotide sequence of the active site is complementary to the nucleotide sequence to be cleaved in a NFATp-encoding mRNA. See, e.g, Cech et al. U.S. Pat. No. 4,987,071 and Cech et al. U.S. Pat. No. 5,116,742. Alternatively, NFATp mRNA can be used to select a catalytic RNA having a specific ribonuclease activity from a pool of RNA molecules. See, e.g., Bartel, D. and Szostak, J. W. (1993) *Science* 261:1411–1418.

Alternatively, NFATp gene expression can be inhibited by targeting nucleotide sequences complementary to the regulatory region of an NFATP gene (e.g, an NFATP promoter and/or enhancer) to form triple helical structures that prevent transcription of an NFATP gene in target cells. See generally, Helene, C. (1991) *Anticancer Drug Des.* 6(6):569–84; Helene, C. et al. (1992) *Ann. N. Acad. Sci.* 660:27–36; and Maher, L. J. (1992) *Bioassays* 14(12):807–15.

ii. Intracellular Antibodies

Another type of inhibitory compound that can be used to inhibit the expression and/or activity of NFATp protein in a cell is an intracellular antibody specific for NFATp discussed herein. The use of intracellular antibodies to inhibit protein function in a cell is known in the art (see e.g, Carlson, J. R. (1988) *Mol. Cell. Biol.* 8:2638–2646; Biocca, S. et al. (1990) *EMBO J.* 9:101–108; Werge, T. M. et al. (1990) *FEBS Letters* 274:193–198; Carlson, J. R. (1993) *Proc. Natl. Acad. Sci. USA* 90:7427–7428; Marasco, W. A. et al. (1993) *Proc. Natl. Acad. Sci. USA* 90:7889–7893; Biocca, S. et al. (1994) *Bio/Technology* 12:396–399; Chen, S-Y. et al. (1994) *Human Gene Therapy* 5:595–601; Duan, L et al. (1 994) *Proc. Natl. Acad. Sci. USA* 91:5075–5079; Chen, S-Y. etal. (1994) *Proc. Natl. Acad. Sci. USA* 91:5932–5936; Beerli, R. R. et al. (1994) *J. Biol. Chem.* 269:23931–23936; Beerli, R. R. et al. (1994) *Biochem. Biophys. Res. Commun.* 204:666–672; Mhashilkar, A. M. et al. (1995) *EMBO J.* 14:1542–1551; Richardson, J. H. et al. (1995) *Proc. Natl. Acad. Sci. USA* 92:3137–3141; PCT Publication No. WO 94/02610 by Marasco et al.; and PCT Publication No. WO 95/03832 by Duan et al.).

To inhibit protein activity using an intracellular antibody, a recombinant expression vector is prepared which encodes the antibody chains in a form such that, upon introduction of the vector into a cell, the antibody chains are expressed as a functional antibody in an intracellular compartment of the cell. For inhibition of transcription factor activity according to the inhibitory methods of the invention, preferably an intracellular antibody that specifically binds the transcription factor is expressed within the nucleus of the cell. Nuclear expression of an intracellular antibody can be accomplished by removing from the antibody light and heavy chain genes those nucleotide sequences that encode the N-terminal hydrophobic leader sequences and adding nucleotide sequences encoding a nuclear localization signal at either the N- or C-terminus of the light and heavy chain genes (see e.g., Biocca, S. et al. (1990) *EMBO J.* 9:101–108; Mhashilkar, A. M. et al. (1995) *EMBO J.* 14:1542–1551). A preferred nuclear localization signal to be used for nuclear targeting of the intracellular antibody chains is the nuclear localization signal of SV40 Large T antigen (see Biocca, S. et al. (1990) *EMBO J.* 9:101–108; Mhashilkar, A. M. et al. (1995) *EMBO J.* 14:1542–1551).

To prepare an intracellular antibody expression vector, antibody light and heavy chain cDNAs encoding antibody chains specific for the target protein of interest, e.g., NFATp protein, is isolated, typically from a hybridoma that secretes a monoclonal antibody specific for NFATp protein. Preparation of antisera against NFATp protein has been described in the art (see e.g., Rao et al, U.S. Pat. No. 5,656,452). Anti-NFATp protein antibodies can be prepared by immunizing a suitable subject, (e.g., rabbit, goat, mouse or other mammal) with a NFATp protein immunogen. An appropriate immunogenic preparation can contain, for example, recombinantly expressed NFATp protein or a chemically synthesized NFATp peptide. The preparation can further include an adjuvant, such as Freund's complete or incomplete adjuvant, or similar immunostimulatory compound. Antibody-producing cells can be obtained from the subject and used to prepare monoclonal antibodies by standard techniques, such as the hybridoma technique originally described by Kohler and Milstein (1975, *Nature* 256:495–497) (see also, Brown et al. (1981) *J. Immunol* 127:539–46; Brown et al. (1980) *J Biol. Chem.* 255:4980–83; Yeh et al. (1976) *PNAS* 76:2927–3 1; and Yeh et al. (1 982) *Int. J. Cancer* 29:269–75). The technology for producing monoclonal antibody hybridomas is well known (see generally R. H. Kenneth, in *Monoclonal Antibodies: A New Dimension In Biological Analyses,* Plenum Publishing Corp., New York, N.Y. (1980); E. A. Lerner (1981) *Yale J. Biol. Med.,* 54:387–402; M. L. Gefter et al. (1977) *Somatic Cell Genet.,* 3:231–36). Briefly, an immortal cell line (typically a myeloma) is fused to lymphocytes (typically splenocytes) from a mammal immunized with a NFATp protein immunogen as described above, and the culture supernatants of the resulting hybridoma cells are screened to identify a hybridoma producing a monoclonal antibody that binds specifically to the NFATp protein. Any of the many well known protocols used for fusing lymphocytes and immortalized cell lines can be applied for the purpose of generating an anti-NFATp protein monoclonal antibody (see, e.g., G. Galfre et al. (1977) *Nature* 266:550–52; Gefter et al. *Somatic Cell Genet.,* cited supra; Lemer, *Yale J. Biol. Med.,* cited supra; Kenneth, *Monoclonal Antibodies,* cited supra). Moreover, the ordinary skilled artisan will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody that specifically binds the maf protein are identified by screening the hybridoma culture supernatants for such antibodies, e.g., using a standard ELISA assay.

Alternative to preparing monoclonal antibody-secreting hybridomas, a monoclonal antibody that binds to a NFATp can be identified and isolated by screening a recombinant combinatorial immunoglobulin library (e.g., an antibody phage display library) with the protein, or a peptide thereof, to thereby isolate immunoglobulin library members that bind specifically to the protein. Kits for generating and screening phage display libraries are commercially available (e.g., the Pharmacia *Recombinant Phage Antibody System,* Catalog No. 27–9400-01; and the Stratagene SurZAP™ Phage Display Kit, Catalog No. 240612). Additionally, examples of methods and compounds particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al International Publication No.

WO 92/01047; Garrard et al. International Publication No. WO 92/09690; Fuchs et al. (1991) *Bio/Technology* 9:1370–1372; Hay et al. (1992) *Hum Antibod Hybridomas* 3:81–85; Huse et al. (1989) *Science* 246:1275–1281; Griffiths et al. (1993) *EMBO J.* 12:725–734; Hawkins et al. (1992) *J Mol Biol* 226:889–896; Clarkson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; Barbas et al. (1991) *PNAS* 88:7978–7982; and McCafferty et al. *Nature* (1990) 348:552–554.

Once a monoclonal antibody of interest specific for NFATp has been identified (e.g., either a hybridoma-derived monoclonal antibody or a recombinant antibody from a combinatorial library, including monoclonal antibodies to NFATp that are already known in the art), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, CDNA encoding the light and heavy chains can be recovered from the display package (e.g., phage) isolated during the library screening process. Nucleotide sequences of antibody light and heavy chain genes from which PCR primers or cDNA library probes can be prepared are known in the art. For example, many such sequences are disclosed in Kabat, E. A., et al. (1991) *Sequences of Proteins of Immunological Interest, Fifth Edition*, U.S. Department of Health and Human Services, NIH Publication No. 91-3242 and in the "Vbase" human germline sequence database.

Once obtained, the antibody light and heavy chain sequences are cloned into a recombinant expression vector using standard methods. As discussed above, the sequences encoding the hydrophobic leaders of the light and heavy chains are removed and sequences encoding a nuclear localization signal (e.g., from SV40 Large T antigen) are linked in-frame to sequences encoding either the amino- or carboxy terminus of both the light and heavy chains. The expression vector can encode an intracellular antibody in one of several different forms. For example, in one embodiment, the vector encodes full-length antibody light and heavy chains such that a full-length antibody is expressed intracellularly. In another embodiment, the vector encodes a full-length light chain but only the VH/CH1 region of the heavy chain such that a Fab fragment is expressed intracellularly. In the most preferred embodiment, the vector encodes a single chain antibody (scFv) wherein the variable regions of the light and heavy chains are linked by a flexible peptide linker (e.g., (Gly$_4$Ser)$_3$) and expressed as a single chain molecule. To inhibit transcription factor activity in a cell, the expression vector encoding the NFATp-specific intracellular antibody is introduced into the cell by standard transfection methods as described hereinbefore.

iii. NFATp-Derived Peptidic Compounds

In another embodiment, an inhibitory compound of the invention is a peptidic compound derived from the NFATp amino acid sequence. In particular, the inhibitory compound comprises a portion of NFATp (or a mimetic thereof) that mediates interaction of NFATp with a target molecule such that contact of NFATp with this peptidic compound competitively inhibits the interaction of NFATp with the target molecule. In a preferred embodiment, the peptide compound is designed based on the region of NFATp that mediates interaction of NFATp with calcineurin. As described in Avramburu et al., (1998) *Mol. Cell.* 1:627–637 (expressly incorporated herein by reference), a conserved region in the amino terminus of NFAT proteins mediates interaction of the NFAT proteins with calcineurin and peptides spanning the region inhibit the ability of calcineurin to bind to and phosphorylate NFAT proteins, without affecting the phosphatase activity of calcineurin against other substrates. Moreover, when expressed intracellularly, peptides spanning this region inhibits NFAT dephosphorylation, nuclear translocation and NFAT-mediated gene expression in response to stimulation, thereby inhibiting NFAT-dependent functions. The region of NFATp mediating interaction with calcineurin contains the conserved amino acid motif: Ser-Pro-Arg-Ile-Glu-Ile-Thr (SEQ ID NO:1).

In a preferred embodiment, a NFATp inhibitory compound is a peptidic compound, which is prepared based on a calcineurin-interacting region of NFATp. A peptide can be derived from the calcineurin-interacting region of NFATp having an amino acid sequence that comprises the 9 amino acid motif of SEQ ID NO: 1. Alternatively, longer regions of human NFATp can be used such as a peptide that comprises the 25 amino acids of SEQ ID NO: 2 (which spans the motif of SEQ ID NO: 1) or the 13 amino acids of SEQ ID NO: 3 (which also spans the motif of SEQ ID NO: 1).

The peptidic compounds of the invention can be made intracellularly in cartilage cells by introducing into the cartilage cells an expression vector encoding the peptide. Such expression vectors can be made by standard techniques, using, for example, oligonucleotides that encode the amino acid sequences of SEQ ID NO: 1, SEQ ID NO: 2 or SEQ ID NO: 3. The peptide can be expressed in intracellularly as a fusion with another protein or peptide (e.g., a GST fusion). Alternative to recombinant synthesis of the peptides in the cells, the peptides can be made by chemical synthesis using standard peptide synthesis techniques. Synthesized peptides can then be introduced into cells by a variety of means known in the art for introducing peptides into cells (e.g, liposome and the like). Recombinant methods of making NFATp inhibitory peptides, and methods using them to inhibit NFATp activity in cells, are described further in Avramburu et al., (1998) *Mol. Cell.* 1:627–637.

It also has been demonstrated that the region of NFATp that interacts with calcineurin is necessary for nuclear import of NFATp and for effective recognition and dephosphorylation such that mutation of this region inhibits NFATp activity (see Avramburu et al., (1998) *Mol. Cell.* 1:627–637). Thus, in another embodiment, NFATp activity can be inhibited by mutating the calcineurin-binding region in the amino terminus, comprising the motif of SEQ ID NO: 1. An example of a mutated sequence of this motif that with greatly reduced ability to interact with calcineurin is shown in SEQ ID NO: 4. The wildtype NFATp amino acid can be modified to the mutated sequence to create a mutated form of NFATp with reduced activity.

Other inhibitory agents that can be used to specifically inhibit the activity of an NFATp protein are chemical compounds that directly inhibit NFATp activity or inhibit the interaction between NFATp and target molecules. Such compounds can be identified using screening assays that select for such compounds, as described in detail above.

B. Stimulatory Compounds

Since downregulation of NFATp activity is associated with increased cartilage cell growth and/or differentiation, a compound that specifically stimulates NFATp activity can be used to inhibit cartilage cell growth and/or differentiation. In the stimulatory methods of the invention, a subject is treated with a stimulatory compound that stimulates expression and/or activity of a NFATp. The methods of the invention using NFATp stimulatory compounds can be used in the treatment of disorders in which cartilage growth and/or differentiation is enhanced, promoted, stimulated, upregulated or the like. As demonstrated in Example 5, tumors that develop in NFATp deficient mice display characteristics of chondrosarcomas. Accordingly, a preferred disorder for treatment using a stimulatory compound of the invention is a chondrosarcoma. Other disorders associated with increased cartilage growth and/or differentiation that may benefit from the stimulatory methods of the invention include osteochondromas, chondromyxoid fibromas, chondromas, enchondromas, chondroblastomas, osteoblastomas, fibrous dysplasias, ossifying fibromas, osteosarcomas and osteocartilaginous exostosis.

Examples of stimulatory compounds include active NFATp protein, expression vectors encoding NFATp and chemical agents that specifically stimulate NFATp activity.

A preferred stimulatory compound is a nucleic acid molecule encoding NFATp, wherein the nucleic acid molecule is introduced into the subject (e.g., cartilage cells of the subject) in a form suitable for expression of the NFATp protein in the cells of the subject. For example, an NFATp cDNA (full length or partial NFATp cDNA sequence) is cloned into a recombinant expression vector and the vector is transfected into the cartilage cell using standard molecular biology techniques. The NFATp cDNA can be obtained, for example, by amplification using the polymerase chain reaction (PCR) or by screening an appropriate cDNA library. The nucleotide sequences of NFATp cDNA is known in the art and can be used for the design of PCR primers that allow for amplification of a cDNA by standard PCR methods or for the design of a hybridization probe that can be used to screen a cDNA library using standard hybridization methods.

Following isolation or amplification of NFATp cDNA, the DNA fragment is introduced into a suitable expression vector, as described above. Nucleic acid molecules encoding NFATp in the form suitable for expression of the NFATp in a host cell, can be prepared as described above using nucleotide sequences known in the art. The nucleotide sequences can be used for the design of PCR primers that allow for amplification of a cDNA by standard PCR methods or for the design of a hybridization probe that can be used to screen a cDNA library using standard hybridization methods.

Another form of a stimulatory compound for stimulating expression of NFATp in a cell is a chemical compound that specifically stimulates the expression or activity of endogenous NFATp in the cell. Such compounds can be identified using screening assays that select for compounds that stimulate the expression or activity of NFATp as described herein.

The method of the invention for modulating aberrant cartilage growth and/or differentiation in a subject can be practiced either in vitro or in vivo (the latter is discussed further in the following subsection). For practicing the method in vitro, cells can be obtained from a subject by standard methods and incubated (i.e., cultured) in vitro with a stimulatory or inhibitory compound of the invention to stimulate or inhibit, respectively, the activity of NFATp. Methods for isolating cartilage cells are known in the art (see e.g., Brittberg et al., (1996) *Clinical Orthopaedics and Related Research* 326; 270–283; Vacanti et al., (1994) *Amer. J Sports Med.* 22; 485–488; Derfus et al., (1996) *Connective Tissue Res.* 35; 337–342; Kim et al., (1993) *Plastic and Reconstructive Surgery.* 94; 580–584; Kandel et al., (1995) *Art Cells Blood Subs and Immob Biotech.* 23; 565–577).

Cells treated in vitro with either a stimulatory or inhibitory compound can be administered to a subject to influence the growth and/or differentiation of cartilage cells in the subject. For example, cartilage cells can be isolated from a subject, expanded in number in vitro by inhibiting NFATp activity in the cells using an inhibitory agent (thereby stimulating the proliferation of the cartilage cells), and then the cartilage cells can be readministered to the same subject, or another subject tissue compatible with the donor of the cartilage cells. Accordingly, in another embodiment, the modulatory method of the invention comprises culturing cartilage cells in vitro with a NFATp modulator and further comprises administering the cartilage cells to a subject to thereby modulate cartilage growth and/or differentiation in a subject. Upon culture in vitro, the cartilage cells can differentiate in to mature articular cartilage and thus the methods encompass administering this mature cartilage to the subject. For administration of cells or cartilage to a subject, it may be preferable to first remove residual compounds in the culture from the cells or cartilage before administering them to the subject. This can be done for example by gradient centrifugation of the cells or by washing of the cartilage tissue. For further discussion of ex vivo genetic modification of cells followed by readministration to a subject, see also U.S. Pat. No. 5,399,346 by W.F. Anderson et al.

In other embodiments, a stimulatory or inhibitory compound is administered to a subject in vivo, such as directly to an articulation site of a subject. For stimulatory or inhibitory agents that comprise nucleic acids (e.g., recombinant expression vectors encoding NFATp, antisense RNA, intracellular antibodies or NFATp-derived peptides), the compounds can be introduced into cells of a subject using methods known in the art for introducing nucleic acid (e.g., DNA) into cells in vivo. Examples of such methods include:

Direct Injection: Naked DNA can be introduced into cells in vivo by directly injecting the DNA into the cells (see e.g., Acsadi et al. (1991) *Nature* 332:815–818; Wolff et al. (1990) *Science* 247:1465–1468). For example, a delivery apparatus (e.g., a "gene gun") for injecting DNA into cells in vivo can be used. Such an apparatus is commercially available (e.g., from BioRad).

Receptor-Mediated DNA Uptake: Naked DNA can also be introduced into cells in vivo by complexing the DNA to a cation, such as polylysine, which is coupled to a ligand for a cell-surface receptor (see for example Wu, G. and Wu, C. H. (1988) *J. Biol. Chem.* 263:14621; Wilson et al. (1992) *J. Biol. Chem.* 267:963–967; and U.S. Pat. No. 5,166,320). Binding of the DNA-ligand complex to the receptor facilitates uptake of the DNA by receptor-mediated endocytosis. A DNA-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Natl. Acad. Sci. USA* 88:8850; Cristiano et al. (1993) *Proc. Natl. Acad. Sci. USA* 90:2122–2126).

Retroviruses: Defective retroviruses are well characterized for use in gene transfer for gene therapy purposes (for a review see Miller, A. D. (1990) *Blood* 76:271). A recombinant retrovirus can be constructed having a nucleotide sequences of interest incorporated into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines include ψCrip, ψCre, ψ2 and ψAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. Nos. 4,868, 116; 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

Adenoviruses: The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89:6482–6486), hepatocytes (Herz and Gerard (1993) *Proc. Natl. Acad. Sci. USA* 90:2812–2816) and muscle cells (Quantin et al. (1992) *Proc. Natl. Acad. Sci. USA* 89:2581–2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use are deleted for all or parts of the viral E1 and E3 genes but retain as much as 80% of the adenoviral genetic material.

Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay.

In preferred embodiments, stimulatory or inhibitory compounds are administered directly to an articulation site of a subject. Examples of articulation sites that can be treated include the ankle, elbow, hip, knee, carpel, metacarpal, pelvis, vertebrae, shoulder, tarsal and wrist. If the stimulatory or inhibitory compounds are chemical compounds that modulate NFATp activity, the stimulatory or inhibitory compounds can be administered to a subject as a pharmaceutical composition. Such compositions typically comprise the stimulatory or inhibitory compounds and a pharmaceutically acceptable carrier. Pharmaceutically acceptable carriers and methods of administration to a subject are described above.

III. Diagnostic Assays

In another aspect, the invention features a method of diagnosing a subject for a disorder associated with aberrant cartilage growth and/or differentiation comprising:
  (a) detecting expression of NFATp in cartilage cells of a subject suspected of having a disorder associated with aberrant cartilage growth and/or differentiation;
  (b) comparing expression of NFATp in cartilage cells of said subject to a control that is not associated with aberrant cartilage growth and/or differentiation; and
  (c) diagnosing the subject for a disorder based on a change in expression of NFATp in cartilage cells of the subject as compared to the control.

The "change in expression of NFATp" in cartilage cells of the subject can be, for example, a change in the level of expression of NFATp in cartilage cells of the subject, which can be detected by assaying levels of NFATp mRNA, for example, by isolating cartilage cells from the subject and determining the level of NFATp mRNA expression in the cells by standard methods known in the art, including Northern blot analysis, reverse-transcriptase PCR analysis and in situ hybridizations. Alternatively, the level of expression of NFATp in cartilage cells of the subject can be detected by assaying levels of NFATp protein, for example, by isolating cartilage cells from the subject and determining the level of NFATp protein expression by standard methods known in the art, including Western blot analysis, immunoprecipitations, enzyme linked immunosorbent assays (ELISAs) and immunofluorescence.

In another embodiment, a change in expression of NFATp in cartilage cells of the subject result from one or more mutations (i.e., alterations from wildtype) in the NFATp gene and mRNA leading to one or more mutations (i.e., alterations from wildtype) in the NFATp amino acid sequence of the NFATp protein. In one embodiment, the mutation(s) leads to a form of NFATp with increased activity (e.g., partial or complete constitutive activity). In another embodiment, the mutation(s) leads to a form of NFATp with decreased activity (e.g., partial or complete inactivity). The mutation(s) may change the level of expression of NFATp, for example, increasing or decreasing the level of expression of NFATp in a subject with a disorder. Alternatively, the mutation(s) may change the regulation of NFATp, for example, by the interaction of the mutant NFATp with upstream targets of NFATp, such as calcineurin. The mutation(s) may alter the ability of NFATp to regulate downstream NFATp targets, such as cytokines in a subject with a disorder. Mutations in the nucleotide sequence or amino acid sequences of NFATp can be determined using standard techniques for analysis of DNA or protein sequences, for example for DNA or protein sequencing, RFLP analysis, and analysis of single nucleotide or amino acid polymorphisms.

In preferred embodiments, the diagnostic assay is conducted on a biological sample from the subject, such as a cell sample or a tissue section (for example, a freeze-dried or fresh frozen section of tissue removed from a subject). In another embodiment, the level of expression of NFATp in cartilage cells of the subject can be detected in vivo, using an appropriate imaging method, such as using a radiolabeled anti-NFATp antibody.

In one embodiment, the level of expression of NFATp in cartilage cells of the test subject may be elevated (i.e., increased) relative to the control not associated with the disorder or the subject may express a constitutively active (partially or completely) form of NFATp. This elevated expression level of NFATp or expression of a constitutively active form of NFATp can be used to diagnose a subject for a disorder associated with decreased cartilage growth and/or differentiation. Cartilage cells cultured in vitro with inhibitory compounds which inhibit expression or activity of NFATp and stimulate the growth and/or differentiation of cartilage cells can be administered to the subject with a disorder associated with decreased cartilage growth and/or differentiation or cartilage degradation, such as arthritis (including rheumatoid arthritis and osteoarthritis).

In another embodiment, the level of expression of NFATp in cartilage cells of the subject may reduced (i.e., decreased) relative to the control not associated with the disorder or the subject may express an inactive (partially or completely) mutant form of NFATp. This reduced expression level of NFATp or expression of an inactive mutant form of NFATp can be used to diagnose a subject for a disorder associated with increased cartilage cell growth and/or differentiation. As discussed in Example 5, tumors that develop in NFATp deficient mice display characteristics of chondrosarcomas in humans. Accordingly, reduced levels of expression of NFATp or expression of an inactive mutant form of NFATp in a subject preferably are used in the diagnosis of chondrosarcomas. Other disorders that may be associated with reduced levels of NFATp or expression of an inactive (partially or completely) mutant form of NFATp include osteochondroma, chondromyxoid fibroma, chondroma, enchondroma, chondroblastoma, osteoblastoma, fibrous dysplasia, ossifying fibroma, osteosarcoma and osteocartilaginous exostosis.

V. Kits of the Invention

Another aspect of the invention pertains to kits for carrying out the screening assays, modulatory methods or diagnostic assays of the invention. For example, a kit for carrying out a screening assay of the invention can include a NFATp-deficient mouse, or NFATp-deficient cells thereof, means for determining cartilage growth and/or differentiation and instructions for using the kit to identify modulators of cartilage growth and/or differentiation. In another embodiment, a kit for carrying out a screening assay of the invention can include an indicator composition comprising an NFATp protein, means for determining cartilage growth and/or differentiation and instructions for using the kit to identify modulators of cartilage growth and/or differentiation.

In another embodiment, the invention provides a kit for carrying out a modulatory method of the invention. The kit can include, for example, a modulatory agent of the invention (e.g., NFATp inhibitory or stimulatory agent) in a suitable carrier and packaged in a suitable container with instructions for use of the modulator to modulate cartilage cell growth and/or differentiation.

Another aspect of the invention pertains to a kit for diagnosing a disorder associated with aberrant cartilage growth and/or differentiation in a subject. The kit can include a reagent for determining expression of NFATp (e.g., a nucleic acid probe for detecting NFATp mRNA or an antibody for detection of NFATp protein), a control to which the results of the subject are compared, and instructions for using the kit for diagnostic purposes.

This invention is further illustrated by the following examples which should not be construed as limiting. The contents of all references, patents and published patent applications cited throughout this application are hereby incorporated by reference.

EXAMPLE 1

Construction of NFATp-Deficient Mice and Characterization of Their Long-Term Phenotype To generate mice deficient for NFATp, genomic DNA containing an exon encoding 47 amino acids of the Rel homology domain were targeted for deletion and replaced by an insertion of a neomycin resistance gene. Germline chimeras generated from one gene-targeted embryonic stem (ES) cell clone produced heterozygous mice that were then bred to produce mice homozygous for the disrupted allele, referred to as NFATp−/− mice (for further description on preparation of NFAT−/− mice, see Hodge et al. (1996) *Immunity* 4:397–405). NFATp−/− mice display splenomegaly and hyperproliferation of T and B lymphocytes as well as enhanced formation of Th2 lymphocytes measured by increased IL-4 and IgE production. Mice lacking NFATp appeared healthy and were fertile and development of the skeletal system was normal. However, after approximately 6 months of age, the animals developed progressive difficulty in ambulation accompanied by fixed contractures and a significantly decreased range of joint motion. All affected animals had involvement of the hip joints, but in some female mice, similar changes were also observed in other peripheral joints such as the shoulder, knee and ankle. The phenotype affected 100% of females and approximately one third of males, and symptoms were much more severe in female animals. Radiograms revealed extensive, dense extra-articular calcification and various degrees of joint destruction. No abnormalities were noted in the axial skeleton.

Recapitulation of Endochondral Bone Formation in NFATp−/− Connective Tissue

To further characterize the phenotype of the NFATp deficient mice, light microscopic analysis of tissues were performed. For paraffin sections, bone specimens were fixed in 10% buffered formalin (0.1M PBS, pH 7.4) for 1–2 weeks, decalcified in 25% formic acid for 2–3 weeks, embedded in paraffin, cut into 6 μm sections, and stained with hematoxylin and eosin or safranin O-fast green. For plastic embedded sections, bones were fixed in formalin for 1 week at 4° C., decalcified in 25% formic acid for 2 days at 4° C., dehydrated in increasing concentrations of ethanol and infiltrated and embedded in JB4 (Polysciences, Warrington, Pa.) and sectioned at 3.5 μm thickness. They were stained with 0.5% toluidine blue or safranin O-fast green.

Skeletal morphogenesis of long bones occurs when undifferentiated mesenchymal stem cells differentiate into chondroblasts that synthesize a cartilage matrix. The central portion of this cartilaginous matrix is resorbed to form the marrow cavity (cavitation). The more superficial cartilage cells at the ends of the long bones further differentiate and synthesize the matrix components of the surface and superficial layers of the true articular cartilage. A second group of cartilage cells distally also proliferates and undergoes a progressive differentiation and synthesis of a cartilage matrix which calcifies and is ultimately resorbed and replaced by osteoblasts to form bone (endochondral ossification).

In NFATp−/− mice, visual inspection of the hip joint revealed abnormalities of the articular cartilage and also revealed extra-articular masses of cartilage that were not only spatially distinct from one another in the extra-articular soft tissues but were easily separable manually from the joint. The articular cartilage in NFATp−/− mice was grayish in color as compared to wt littermates and had a visibly roughened surface in contrast to the smooth, polished appearance of the wildtype control articular cartilage. Low power, 20×, examination of the femoral heads and acetabulae of 12 month old control +/− and NFATp−/− mutant mice, showed thickening of articular cartilage and sites of extra-articular cartilage cell proliferation and joint destruction in the mutant animal. High power (200×) of the mutant mice showed invasion of the acetabulum by proliferating cartilage cells and obliteration of the joint space with loss of Safranin-O staining (*). Femoral head and extra-articular connective tissues of three month old NFATp−/− mouse, 100×, clearly demonstrated the physical separation of the sites of articular and extra-articular cartilage proliferation. Extra-articular connective tissues of three month old NFATp−/− mouse demonstrated the differentiation of resident cells into ordered columnar cartilage. Extra-articular connective tissues of six month old NFATp−/− mouse showed calcification of cartilage and the beginnings of endochondral ossification in the extra-articular soft tissue.

Thus, histologic analysis demonstrated proliferation of abnormal-looking cartilage cells in the articular cartilage most apparent in older female animals. When this proliferation occurred, it was apparent in the layer of already existing cartilage cells above the zone of calcified cartilage. In the most severe cases, there was extensive degradation of the cartilage and destruction of the joint.

In all NFATp−/− female mice, ectopic formation of cartilage occurred in the extra-articular soft tissues. In extra-articular connective tissue, resident cells rapidly differentiated to Saffranin-O staining cartilage cells beginning as early as three months of age. Multiple, spatially distinct sites of cartilage formation were formed with time, accompanied by progressive endochondral differentiation of the cartilage cells, columnar arrangement of the tissue, invasion of the cartilage tissue by capillaries and chondroclasts (osteoclasts), calcification of the cartilage and replacement of cartilage by bone synthesized by osteoblasts (endochondral ossification). Thus at three months of age, induction of chondrogenesis in the extra-articular soft tissues occurred with resident cells in the extra-articular soft tissue beginning to differentiate into cartilage and align into typical columnar fashion. At six months of age, sequential differentiation of the chondrocytes and the onset of endochondral ossification were apparent. From 3 to 20 months there was a steady and progressive increase in the volume of cartilage and bone in the individual extra-articular masses as the process of endochondral bone formation continued, as well as the initiation of new sites of cartilage induction. The uncontrolled induction, proliferation and differentiation of the resident extra-articular connective tissue cells over the 20 month period studied also extended into and between the fibers of the overlying muscle layers.

EXAMPLE 2

Preparation of Chondrogenic Cells from NFATp Deficient Mice

The proliferating cartilage cells in the joint varied in size but were usually very large, had increased chromatin content, noticeable mitotic figures and were safranin O positive. To more carefully characterize the phenotype of these cells, cartilaginous tissue was scraped from the surfaces of the acetabulum, glenoid and femoral and humeral heads of affected NFATp−/− mice and wildtype (wt) littermates and cultured in vitro. To isolate chondrogenic cells, the hind limbs of wild type or NFATp−/− mice were dissected from the torso leaving the femoral joint intact. The femoral head was isolated from the joint and the articular surface was cut upwards from the neck of the femur. The articular cap was released by producing a small incision through the femoral head and applying pressure with a pair of forceps to release the secondary center of underlying trabecular bone. Cells within the articular cartilage that had been cleanly removed free of the underlying trabecular bone were dissociated by digestion of the tissue with trypsin\collagenase for 6 hours as described in Gerstenfeld, L. C. et al., (1989) *J. Biol. Chem.* 264: 5112–5120. Cartilage cells were plated at the density of $2.5 \times 10^5$ cells per 100 mm tissue culture dish and grown in DMEM 10% fetal bovine serum until reaching confluence at 2–3 weeks. The confluent cartilage cells were trypsinized and re-plated at a density of $2 \times 10^6$ cells per 100 mm tissue culture dish. All experiments described in these studies are from second passage primary cells.

In contrast to the slow growth of cartilage cells observed in cultures established from wt mice, cultures established from NFATp−/− mice expanded rapidly, necessitating frequent passaging. Examination of these cultures at low cell density revealed two types of cells, a spindle-shaped mesenchymal-appearing cell and a cuboidal cell that grew in sheets typical of chondroblasts. However, as the cultures became confluent, all cells assumed a cuboidal shape.

EXAMPLE 3

Demonstration of Aberrant NFATp mRNA Expression in Cartilage Cells of NFATp-Deficient Mice To confirm that NFATp mRNA expression in the cartilage cells of the NFATp−/− mice was from the disrupted NFATp gene, expression of NFATp in mRNA in cultured cartilage cells of wild type and NFATp−/− mice was determined by reverse-transcriptase polymerase chain reaction (RT-PCR) analysis. Cartilage cells were harvested as described above and RNA isolated by standard methods. RT-PCR was performed on the isolated RNA using primers specific for NFATp. Primers specific for HPRT were used as a control.

The results of RT-PCR analysis of mRNA expression in wild type and NFATp−/− cartilage cells are shown in FIG. 1. Analysis of the wild type cartilage cells revealed the presence of transcripts encoding NFATp (see FIG. 1, lane 1). A mutant transcript corresponding in size to the gene targeted NFATp allele was detected in the NFATp−/− cultured cells (see FIG. 1, lane 2).

EXAMPLE 4

Cultured NFATp−/− Cartilage Cells Express Antigens Characteristic of Mature Cartilage Cells To further analyze the phenotype of the cartilage cells from the NFATp deficient mice, immunohistochemical analysis was performed. Immunofluorescent staining was carried out with antibodies to type II collagen (PF4Z, Caltag) and cartilage oligomeric protein (COMP) antibody (kindly provided by Dr. R. Heinegard). Immunoreactions were carried out as previously reported using culture pretreatment with monesin to enhance cellular staining of secreted proteins (see Toma, C. et al. (1997) *J. Bone & Miner. Research* 12: 2024–2039). Both phase contrast and immunofluorescent photomicroscopy were performed using an Olympus Microscope OM-2 (Olympus Co. Lake Purchase, NY) on Kodak T Max p3200 film (Eastman Kodak Co., Rochester, N.Y.). An anti-NFATp mAb specific for the amino terminus of NFATp (4G5-G6, gift of G. Crabtree) was used as ascites at 1:250 dilution in Tris Buffered Saline (TBS). A control isotype antibody and no primary antibody were used as controls. Immunohistochemistry was performed according to established techniques.

Figure 2A:
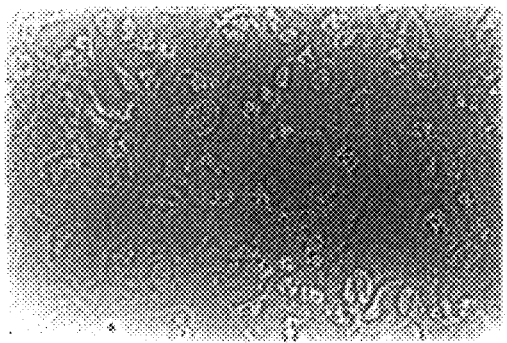
FIG. 2a is a phase contrast photograph of NFATp−/− cartilage cells.
Figure 2B:
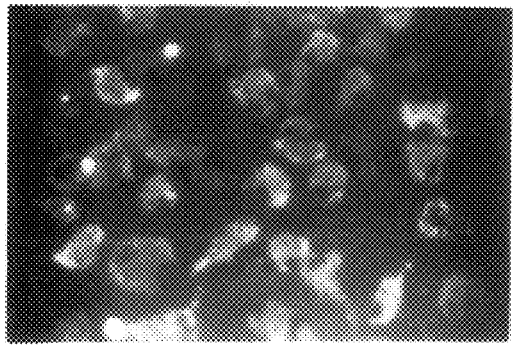
FIG. 2b is a photograph of the same field of NFATp−/− cartilage cells shown in FIG. 2a stained with an antibody to Type II collagen.
Figure 2C:
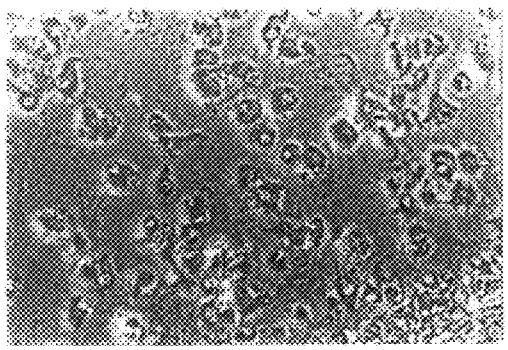
FIG. 2c is a phase contrast photograph of NFATp−/− cartilage cells.
Figure 2D:
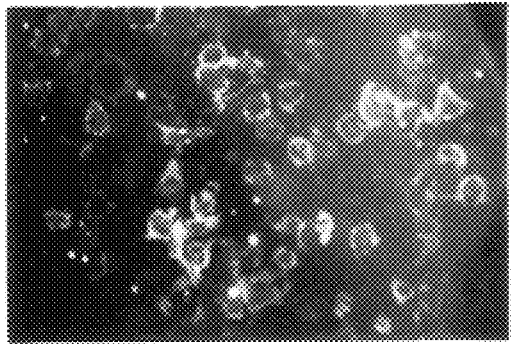
FIG. 2d is a photograph of the same field of NFATp−/− cartilage cells shown in FIG. 2b stained with anti-cartilage oligomeric protein (COMP) antibody.

The results of the immunohistochemical staining with antibodies to Type II collagen and COMP are shown in FIGS. 2A–2D. FIGS. 2A and 2C are phase contrast photographs of NFATp−/− cartilage cells. FIGS. 2B and 2D are photographs of the same fields as FIGS. 2A and 2C, respectively, stained with either anti-Type II collagen antibody (FIG. 2B) or anti-COMP antibody (FIG. 2D). This immunohistochemical analysis confirmed that a high percentage of the cultured NFATp−/− cartilage cells expressed type II collagen and cartilage oligomeric protein (COMP), antigens which are characteristic of mature cartilage cells.

EXAMPLE 5

Tumors Observed in NFATp Deficient Mice Display Characteristics of Chondrosarcomas There has been controversy on what constitutes malignancy in cartilage tumors in humans. In this example, the proliferative capacity and karyotype of cartilage cells from NFATp−/− mice was examined. Several pieces of data suggest that the tumors observed in NFATp-deficient animals may be chondrosarcomas.

First, the large size and varied appearance of the proliferating cartilage cells coupled with their invasion of the acetabulum and adjacent connective tissue strongly suggests a malignant process, particularly as it is accompanied by the induction and uncontrolled proliferation of cartilage in the surrounding connective tissue.

Figure 3:
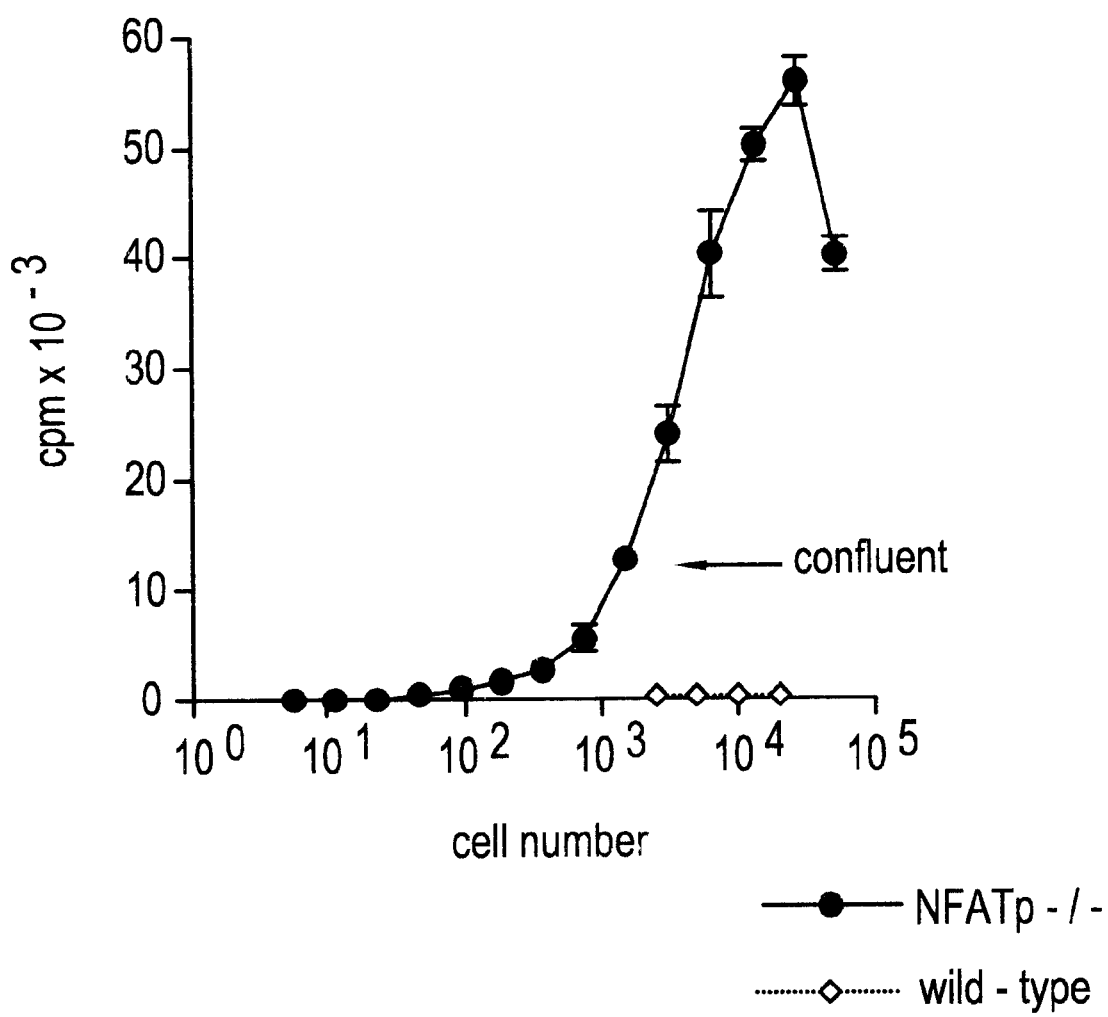
FIG. 3 is a graph depicting continued in vitro proliferation of cultured cartilage cells derived from NFATp−/− mice.

Second, in contrast to wt cartilage cells, NFATp−/− tumor cells did not display contact-induced growth inhibition since they continued to proliferate in vitro even when plated at confluency (illustrated in the graph of FIG. 3). Wt cartilage cells, in contrast, had less than 500 cpm proliferation at all cell numbers plated. The proliferation assays were performed by plating wild type cartilage cells and NFATp-deficient tumor cells at varying densities in triplicate in 96 well microtiter plates for 48 hours and pulsing them with $^3$H-thymidine 16 hours prior to harvesting to measure incorporation into DNA.

Third, karyotypic analysis of four tumor cell lines established from NFATp−/− mice revealed aneuploidy in three of them. Karyotypic analysis was performed by Diagnostic Cytogenetics, Inc. (Seattle, Wash.) by standard methods. The results are summarized below in Table 1.

TABLE 1

Cytogenetic analysis of NFATp(−/−) cartilage cell lines

| Tumor | Karyotype |
|---|---|
| 1 | 40,XY |
| 2 | 40–41,XX[cp7]/39–40,XX–4[6], −12[7],+17[2],+mar[5][cp7]/ 43,X,der(?X),add(1),der(?6),+?7,+9,+mar5[3] |
| 3 | 40,X–X,+mar[3]/39,X–X,–14,+mar[2]/41,XX+mar[4]/40,XX[41] |
| 4 | 71–89,XXXX–2[6],–3[10],–4[12],–4[10], –6[2],–7[8],–9[6],–10[2],–11[4],–12[3],–13[2], –14[3],–15[2],–16[12],–17[2],+18[4],+1–6mar[9][cp12] | mar = marker
der = derivative
add = additional material of unidentified origin

The first line was a normal male with random chromosome loss. The second line had a modal chromosome number of 40 in 7 cells with monsomy of chromosomes 4 and 12, trisomy of chromosome 17 and gain of markers in most of the cells. An additional 3 cells displayed additional structures and numerical abnormalities. Two clones were observed in the third tumor, a normal 40XX clone in 41 cells and an abnormal clone that demonstrated clonal evolution. A marker chromosome was observed in all cells in the clone, and in addition, 5 cells demonstrated loss of an X and 2 of these also had loss of chromosome 14. The fourth tumor was pseudotetraploid with a modal chromosome number of 71–76 (range 71–89), with a consistent finding of loss of chromosomes 4 and 16. One to 6 marker chromosomes were observed in most cells and there were no normal diploid or tetraploid cells.

The histologic picture coupled with the loss of contact inhibition and the presence of aneuploidy suggests that the tumors arising in NFATp deficient mice may be best classified as chondrosarcomas, although a pathologic survey of lungs, brain and intestine did not reveal metastastic lesions. It should be noted that NFATp mutant cartilage cells do retain a differentiated phenotype similar to some, but not all, human chondrosarcomas.

EXAMPLE 6

The Transcription Factor NFATp is a Repressor of Chondrogenesis

The following experimental procedures were used in Example 6:

Mice. NFATp−/− mice were generated as described (Hodge, M. R., et al. 1996. Immunity 4, 1–20.; Ranger, A. M., et al. 1998. Nature 392, 186–190.) and have been backcrossed onto a BALB/c background for at least 8 generations. Wild-type controls were +/+ or +/−littermates. Mice were housed in sterilized microisolator cages, fed autoclaved food and water, and handled in laminar airflow hoods.

Light Microscopic analysis. For paraffin sections, bone specimens were fixed in 10% buffered formalin (0.1M PBS, pH7.4) for 2 weeks, decalcified in 25% formic acid for 2–3 weeks, processed and embedded in paraffin, cut into 6 □m sections, and stained with hematoxylin and eosin or safranin O-fast green. For plastic embedded sections, bones were fixed and decalcified as above and infiltrated for 2–3 weeks prior to embedding in JB4 medium (Polysciences, Warrington, Pa.) and sectioned at 4.5 □m thickness (Clauss, I. M., et al. 1993. Developmental Dynamics 197, 146–156.). They were stained with 0.5% toluidine blue or safranin O-fast green.

Preparation of Cartilage Cells and Cell Lines and Stable Transfection of the S12 and EA Cartilage Cell Lines. Hind limbs of normal and NFATp−/− and +/− mutant mice were dissected from the torso leaving the femoral joint intact. The femoral head was isolated from the joint and the articular surface was cut upwards from the neck of the femur. The articular cap was released by producing a small incision through the femoral head and applying pressure with a pair of forceps to release the secondary center of ossification containing trabecular bone. Cells within the articular cartilage that had been cleanly removed free of the underlying trabecular bone or cells from physically distinct masses in the extra-articular soft tissues (EA cells) were dissociated by digestion of the tissue with trypsin\collagenase (Gerstenfeld, L. C., et al. 1989. J. Biol. Chem. 264, 5112–5120.) for 6 h. Cells were plated at a density of 2.5×105 per 100 mm dish and grown in DMEM 10% fetal bovine serum until reaching confluence at 2–3 weeks. Cells were trypsinized and replated at $2\times10^6$ per 100 mm dish. All experiments depicted in these studies are from second passage primary cells.

To generate the S12 cell line, rapidly dividing cultures of NFATp−/− primary cells that had reached confluence were subcloned by limiting dilution (1000 cells/100 mm dish) and allowed to grow until separate colonies could be visualised. Colonies were picked with cloning discs (Scienceware, Bel-art Products, NJ) and expanded to establish multiple clonal lines One such line, S12, was chosen for further study. Stable transfection of S12 and of a bulk population of EA cells was achieved by electroporation at 250V, 975 uF of 5×106 S12 or EA cells in 400 ul RPMI 1640 media without supplements containing 20 □g of an NFATp expression plasmid in the vector pRep4, or empty vector alone. Selection with hygromycin at 25–50 □g/ml resulted in the appearance of hygromycin resistant colonies in approximately 2 weeks.

Immunohistochemistry Analysis. Immunofluoresent staining was carried out with antibodies to type II collagen (PF4Z, Caltag) and cartilage oligomeric protein (COMP), kindly provided by Dr. R. Heinegard. Immunoreactions were carried out as previously reported using culture pre-treatment with monesin to enhance cellular staining of secreted proteins (Toma, C., et al. 1997. J. Bone & Miner. Research 12, 2024–2039.). Both phase contrast and immunofluoresent photomicroscopy were performed using an Olympus Microscope OM-2 (Olympus Co. Lake Purchase, NY) on Kodak T Max p3200 film [Eastman Kodak Co., Rochester, N.Y.].

RT-PCR, Northern and Western blot analysis. RNA was prepared from wt and NFATp−/− cartilage cultures and from S12 and EA transfected cell lines. RT-PCR was performed using primers specific for NFATp (upper 5' tctccaatcagtcgggctcctatg (SEQ ID NO:5), lower 5' gctcggggcagtctgttgttgg) (SEQ ID NO:6), NFATc (upper 5'tccggcgcatgcgagccgtcatcgactgtgctgggatcctga (SEQ ID NO:7), lower 5'ggacccgggtcaattggcaggaaggtacgtgaaacg) (SEQ ID NO:8), NFAT4 (upper 5'cttccccagcagcctctcatcc (SEQ ID NO:9), lower 5'ccgtggtgggcaaaaggctcagtg) (SEQ ID NO:10), NFAT3 (upper 5'gaagctaccctccggtacagag (SEQ ID NO:11) lower 5'gcttcatagctggctgtagcc) (SEQ ID NO:12), type II collagen (upper 5'cctgtctgcttcttgtaaaac (SEQ ID NO:13), lower 5'acagaggtgtttgacacag) (SEQ ID NO14), type X collagen (upper 5'cttctcaggattcctagtggc (SEQ ID NO:15), lower 5'gagccattgagtgatgcacc) (SEQ ID NO:16), CDMP-1 (GDF-5) (upper 5'acgggacctgttctttaatg (SEQ ID NO:17), lower 5'cttatacaccacgttgttgg) (SEQ ID NO:18), □-actin (upper 5'ctggagaagagctatgagct (SEQ ID NO:19), lower 5'gccatgccaatgttgtctct) (SEQ ID NO:20) and HPRT (Gerstenfeld, L. C., et al. 1989. J. Biol. Chem. 264, 5112–5120.; Metsaranta, M., et al. 1991. Biochem. Biophys. Acta 1089, 241–243.; Elima, K., et al. 1993. Biochem. J. 289, 247–253.; Chang, S. C., et al. 1994. J. Biol. Chem. 45, 28227–28234.). All RT-PCR was carried out using 1 µg of total mRNA using a Titan One Tube kit (Boehringer Mannheim) according to manufacturer's instructions. Individual salt and primer annealing temperatures were determined for each primer set. For semi-quantitative RT-PCR initial RT reactions were carried out followed by sequent amplification for five cycles. The resultant cDNAs were then diluted serially 3 times and PCR carried out for 24 cycles. Amplicons from control reactions carried out with mRNA isolated from articular cartilage were confirmed by sequence analysis. The products were resolved on a 1.4% agarose gel, stained with gel star and individual band intensities determined using an Alpha Innotech Image Analysis system. The slopes of the titration curves normalized to that of β-actin were used as a relative approximation of the individual mRNA quantities.

For Northern blot analysis 10 µg of RNA was fractionated by electrophoresis on 1.2% agarose/6% formaldehyde gels. Identical gels were blotted to Gene Screen and hybridized with at least 1×106 cpm of random primer labeled cDNA fragments per ml of QuickHyb solution according to manufacturer's instructions (Stratagene). cDNA fragments were purified from plasmids TGFβ1,2,3 and GDF5,6. Nuclear and cytoplasmic extracts for western blot analysis were prepared from S12 and EA NFATp transfectants. Nuclei were isolated as described (Dolmetsch, R. E., et al. 1997. Nature 386, 855–858.). Extracted proteins were separated by 8% PAGE followed by electrotransfer to nitrocellulose membranes and probed with a mAb specific for NFATp (Santa Cruz Biotechnology) followed by horseradish peroxidase-conjugated goat anti-mouse IgG and enhanced chemiluminescence according to the instructions of the manufacturer (Amersham).

Proliferation assays. Wt cartilage cells and NFATp−/− cartilage cells were plated at varying densities in triplicate in 96 well microtiter plates for 48 hours and pulsed with 3H-Thymidine 16 hours prior to harvesting to measure incorporation into DNA.

Karyotypic analysis and generation of cartilage cells from mesenchymal stem cells in vitro. Karyotypic analysis was performed by K. Au, Diagnostic Cytogenetics, Inc. (Seattle, Wash.). The human and mouse mesenchymal stem cells were generated as described (Lennon, D. P., et al. 1996. In Vitro Cell. Dev. Biol. 32, 602–611.; Pittenger, M. F., et al. 1999. Science 284, 143–147.).

In mice lacking NFATp, resident cells in the extra-articular connective tissues spontaneously differentiate to cartilage. These cartilage cells progressively differentiate and the tissue undergoes endochondral ossification, recapitulating the development of endochondral bone. Proliferation of already existing articular cartilage cells also occurs in some older animals. At both sites, frank transformation of cartilage cells occurs. Consistent with these data, NFATp expression is regulated in mesenchymal stem cells induced to differentiate along a chondrogenic pathway while overexpression of NFATp in cartilage cell lines extinguishes the cartilage phenotype. Thus NFATp is a repressor of cartilage cell growth and differentiation and also has the properties of a tumor suppressor.

Nuclear Factor of Activated T cells (NFAT) is a family of transcription factors critical in regulating early gene transcription in response to T cell receptor-mediated signals in lymphocytes (Durand, D., et al. 1988. Mol. Cell. Biol. 8, 1715–1724.; Shaw, J., et al. 1988. Science 241, 202–205.; Crabtree, G. 1989. Science 249, 355–360.; Rao, A., et al. 1997. 15, 707–747.). There are currently four known NFAT genes, NFATp (NFATc2, NFAT1), NFATc (NFATc1, NFAT2), NFAT3 (NFATc4), NFAT4 (NFATc3, NFATx) (Northrop, J. P., et al. 1994. Nature 369, 497–502.; McCaffrey, P. G., et al. 1993. Science 262, 750–754.; Hoey, T., et al. 1995. Immunity 2, 461–472.; Masuda, E. S., et al. 1995. Mol. Cell. Biol. 15, 2697–2706.; Ho, S. N., et al. 1995. J. Biol. Chem. 270, 19898–19907.) that share homology within a region distantly related to the Rel domain. As described below, evidence is emerging that this family of transcription factors controls processes of cell differentiation, likely in response to changes in calcium flux, in progenitor cells of multiple lineages.

Much has been learned about the function of NFAT proteins from the generation of NFAT genetic mutant mouse strains. Mice lacking NFATc die in utero from failure to form the semilunar cardiac valves (Ranger, A. M., et al. 1998. Nature 392, 186–190.; Luis de la Pompa, J., et al. 1998. Nature 392, 182–186.) and a role for NFAT3 in cardiac hypertrophy has been elegantly demonstrated (Molkentin, J. D., et al. 1998. Cell 93, 215–228.). T cells from mice lacking NFATc in the lymphoid system (as evaluated by RAG-2 blastocyst complementation) hypoproliferate and have impaired IL-4 production (Ranger, A. M., et al. 1998. Immunity 8, 125–134.; Yoshida, H., et al. 1998. Immunity 8, 115–124.) consistent with a function of NFATc as a direct transcriptional activator of the IL-4 gene. Recently, NFATc has also been shown to regulate HIV-1 replication in T cells (Kinoshita, S., et al. 1997. Immunity 6, 235–244. Evidence that NFATp and NFAT4 might repress proliferative responses, Th2 cell formation and lymphocyte activation were obtained from the characterization of NFATp and NFAT4 single and double deficient animals. Mice lacking NFAT4 have normal peripheral T cell proliferation and cytokine production although there is an increase in the number of memory/activated T and B cells (Oukka, M.,et al. 1998. Immunity 9, 295–304). The phenotype of mice lacking NFATp has previously been described (Hodge, M. R., et al. 1996. Immunity 4, 1–20.; Xanthoudakis, S., et al. 1996. Science 272, 892–895.; Kiani, A., et al. 1997 Immunity 7, 849–860.). Such animals display modest splenomegaly with hyperproliferation of T and B lymphocytes and enhanced T helper 2 responses as measured by increased IL-4 and IgE production. Mice lacking both NFATp and NFAT4 have massive lymphoproliferation and selective activation of the Th2 compartment (Ranger, A. M., et al. 1998. Immunity 9, No. 5, 627–635.).

The widespread distribution of NFATp in the adult animal suggested that this family member might control cellular differentiation programs in organ systems unrelated to the immune system, and indeed recent evidence suggests that NFATp may participate in processes of adipogenesis and myogenesis (Ho, I-C., et al. 1998. Proc. Natl. Acad. Sci. USA 95, 15537–15541.; Abbott, K. L., et al. 1998 Molecular Biology of the Cell 10, 2905–2916.). NFATp is a potent repressor of cartilage cell growth and differentiation in the adult animal. Few molecular regulators of chondrogenesis have been identified, and the majority of these affect the embryonic formation of cartilage. To our knowledge, NFATp is the first transcription factor described to control the differentiation of adult mesenchymal stem cells into cartilage. Mice lacking NFATp should prove valuable for the study of cell lineage commitment decisions in chondrogenesis. Further, given the teachings herein, the use of NFATp inhibitors in degenerative and inflammatory joint diseases such as osteoarthritis and rheumatoid arthritis, where cartilage has been destroyed and in the stimulation of endochondral bone formation to achieve repair of bone defects and fractures, is possible.

Proliferation of NFATp−/− Cartilage Cells is Cell-intrinsic

One explanation for this phenotype is induction of uncontrolled cartilage proliferation by an extrinsic factor(s). Alternatively, the dysregulation observed may be intrinsic to the cartilage cell precursor. To determine whether these characteristics were extrinsic or intrinsic to the cells, the phenotype and behavior were carefully characterized. Cartilaginous tissue was removed from the surfaces of the femoral and humeral heads and from the extra-articular cartilage masses of affected NFATp−/−, control wildtype (wt) and NFATp+/− heterozygous mice and placed in culture. NFATp is widely expressed in many adult tissues, but has not been described to be present in cartilage. Examination by RT-PCR of RNA prepared from cells from the cartilage cultures established above did reveal the presence of transcripts encoding NFATp in wildtype cartilage cells. Further, a mutant transcript corresponding in size to the gene targeted NFATp allele was detected in the cells established from NFATp−/− cartilage. Interestingly, transcripts specific for the three other NFAT family members, NFATc, NFAT4 and NFAT3, were also present in wt and NFATp−/− cartilage. Examination of the NFATp−/− cultures revealed cuboidal cells that grew in sheets. Immunohistochemical analysis confirmed that a high percentage of cells expressed type II collagen and cartilage oligomeric protein (COMP), antigens which are characteristic of mature cartilage cells. These results demonstrated that mature cartilage cells expressed NFATp as well as NFATc, NFAT4 and NFAT3 and that the proliferating cells present in the articular and extra-articular cartilage of NFATp−/− animals were indeed of cartilage origin.

Cartilage cells from NFATp−/− mice proliferated in culture, and in some instances displayed uncontrolled growth consistent with malignant transformation (see below). A variety of growth and differentiation factors have been shown to cause induction and proliferation of cartilage cells from primitive mesenchymal progenitor cells in vitro, and in some instances, in vivo. Most notable among these are members of the TGF-β family and the related bone morphogenetic protein factors (BMPs) although the latter appear to be more critical in skeletal morphogenesis than in mature cartilage growth (Wozney, J. M., et al. 1988). Science 242, 1528–1534.; Kingsley, D. M. 1994. Genes Dev. 8, 133–146.). It was possible that NFATp negatively regulated the transcription of one or more of these factors. The NFATp−/− cartilage cell lines were tested for their expression of the TGF-β family members most often thought to be involved in chondrogenesis and found normal or reduced levels of TGFβ1, TGFβ2, TGFβ3, GDF5 (CDMP-1) and GDF6 (CDMP-2) transcripts as compared to wt cartilage cells. Thus, overexpression of these known regulators of chondrogenesis does not appear to account for the induction of proliferation and differentiation of connective tissue precursor cells to cartilage cells or the prolieration of articular cartilage cells observed in the absence of NFATp in the adult animal. To further address the possibility these cellular events were driven by secreted factors, wt cartilage cells were cultured with supernatants derived from the NFATp mutant cell lines. No effect on proliferation of wt cartilage was observed. The uncontrolled induction and proliferation of endochondral lineage cartilage cells and of the already existing articular cartilage cells in the absence of NFATp is likely to be intrinsic to the cell, although a secreted factor that requires other culture conditions to be active may play a role in this process.

NFAT Expression is Regulated During Cartilage Cell Differentiation

Figure 4A:
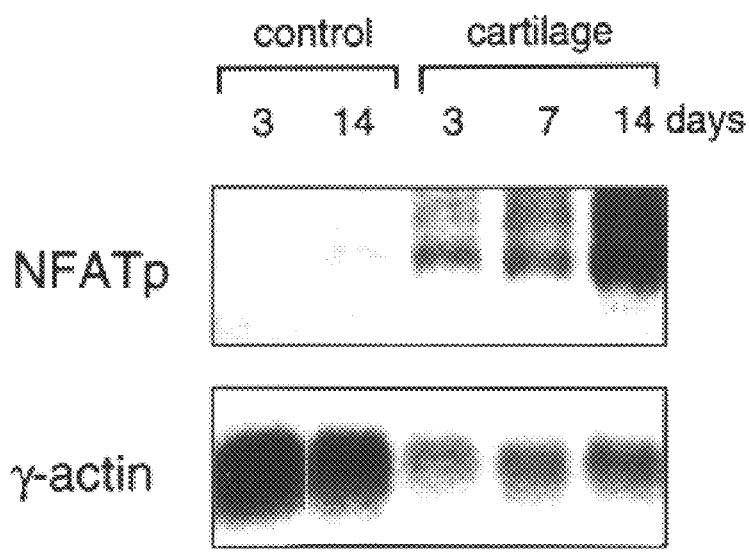
FIG. 4 shows that expression of NFATp is regulated during chondrogenesis. Northern blot analysis of human mesenchymal stem cells undifferentiated or differentiated under chondrogenic (left panel) or osteogenic (right panel) conditions. Expression of NFATp (A), NFATc (B) and actin (C).
Figure 4B:
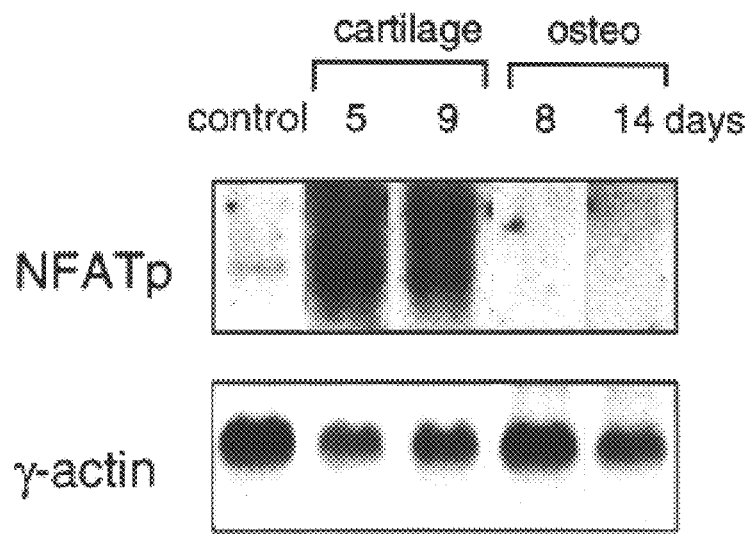

NFATp is not expressed in the skeletal system during embryonic development at E11 and E13.5, and mice lacking NFATp display normal skeletal morphogenesis. Therefore we examined the role of NFATp in controlling cartilage cell differentiation at the level of the adult mesenchymal progenitor cell. Recently Caplan and colleagues have described an in vitro pellet culture system whereby purified mesenchymal stem cells harvested from human or rabbit bone marrow can be differentiated along a chondrogenic or osteogenic lineage (Lennon, D. P.,et al. 1996 Cell. Dev. Biol. 32, 602–611.; Pittenger, M. F., et al. 1999. Science 284, 143–147.; Johnstone, B., et al. 1998. Exp. Cell Res. 238, 265–272.; Mackay, A. M., et al. 1998. Tissue Engineering 4, 415–427.). For chondrogenesis, such cultures rely on the addition of TGF-β and the morphometric constraints of a pellet culture system. The expression of NFAT family members was assessed in human mesenchymal stem cells cultured under chondrogenic conditions (FIG. 4). In bone-marrow-derived stem cells untreated with exogenous growth factors, so-called "control", NFATp transcripts were detectable. By day 3 of differentiation NFATp mRNA levels had markedly increased in stem cells cultured under chondrogenic conditions and by day 14, NFATp transcripts had further increased. In contrast, in stem cells cultured under osteogenic conditions, transcripts for NFATp were not detectable. Thus, levels of NFATp are specifically regulated during chondrogenesis. Transcripts for the three other NFAT family members, NFATc, NFAT4 and NFAT3, were also present in differentiating chondrocytes. However, in contrast to NFATp, their level of expression did not fluctuate during differentiation and was not restricted to the chondrogenic pathway as they were also detected in cultures differentiated along an osteogenic pathway. These data and the in vivo phenotype described above indicate that NFATp expression is regulated in undifferentiated human mesenchymal stem cells during chondrogenesis, and that NFATp is the family member likely to control lineage commitment along this pathway in post embryonic mesenchymal stem cells.

Figure 5A:
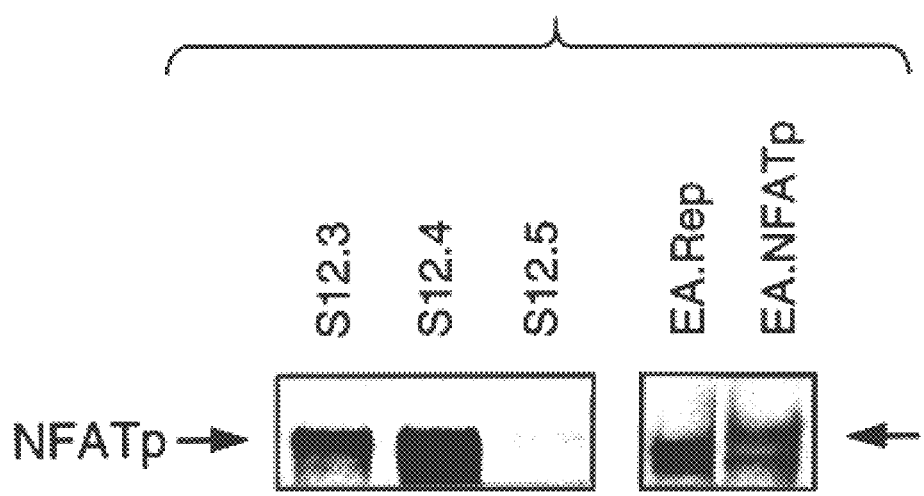
FIGS. 5A and 5B show that overexpression of NFATp represses the cartilage phenotype. Panel A shows western blot analysis of S12 and EA control (Rep) and NFATp transfectants with anti-NFATp antibody. Panel B shows RT-PCR analysis of mature cartilage gene expression of S12 and EA control and NFATp transfectants using Type II collagen, Type X collagen, CDMP-1 and actin primers (Metsaranta et al., 1991; Elima et al., 1993; Chang et al., 1994a).
Figure 5D:
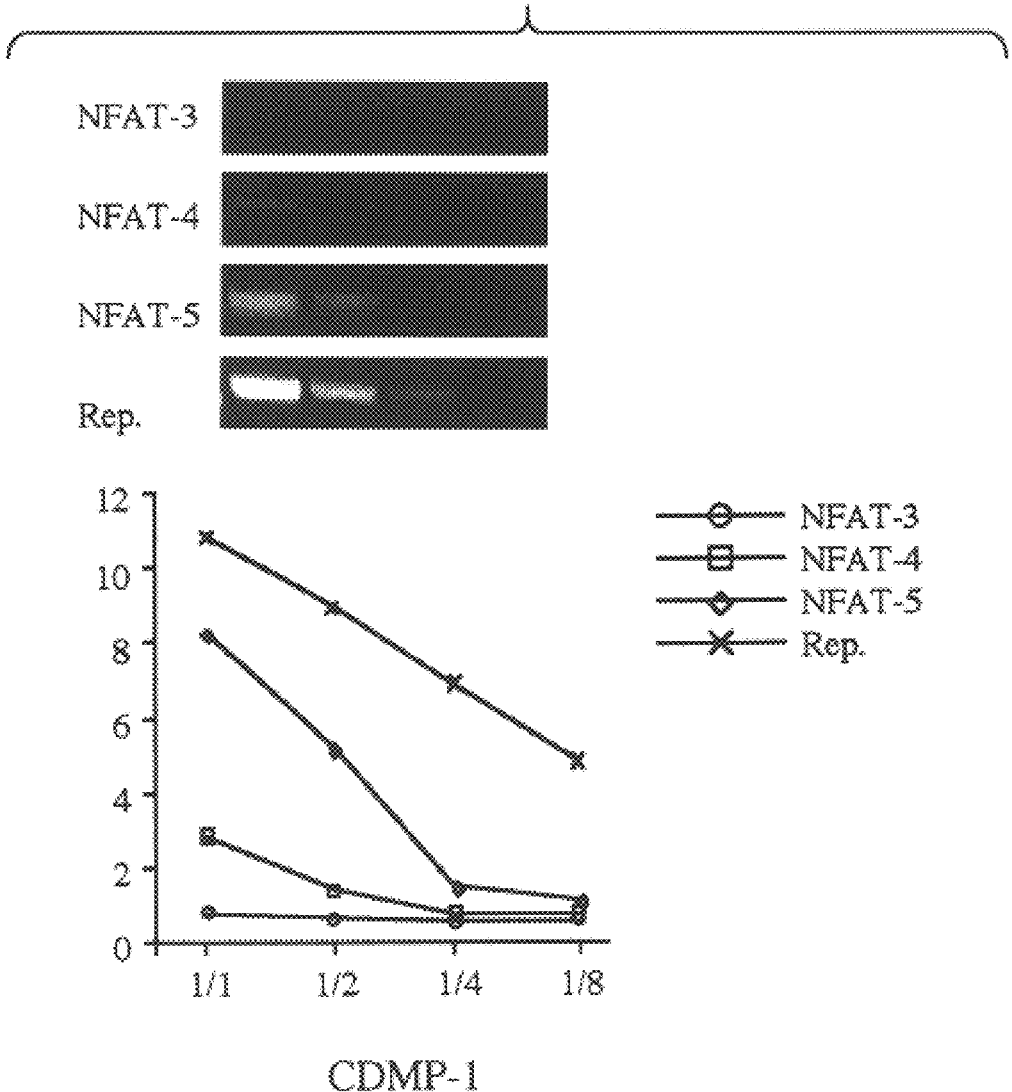

Ectopic Expression of NFATp in Two NFATp−/− Cartilage Cell Lines Derived from Both Articular and Extra-articular Tissues Extinguishes the Cartilage Phenotype The uncontrolled proliferation of resident connective tissue cells and their differentiation to cartilage cells and the proliferation of existing articular cartilage cells, coupled with the regulated expression of NFATp in mesenchymal stem cell cultures suggested that NFATp represses the chondrogenic program. To further investigate this possibility, NFATp was stably introduced into S12 and EA, two cartilage cell lines derived from bulk-cultured NFATp−/− articular cartilage and extra-articular cartilage respectively. Several transfected subcloned S12 lines and bulk-transfected but not subcloned EA lines were derived and analyzed by western blot for expression of NFATp (FIG. 5a). A panel of S12 and EA transfectants expressing different levels of NFATp were then analyzed by semi-quantitative RT-PCR for expression of characteristic cartilage cell markers (FIG. 5b). Expression of Type II collagen, Type X collagen and CDMP-1 were markedly repressed in all of the S12 NFATp transfected sublines, and a rough correlation between levels of NFATp protein and repression of cartilage cell phenotype was observed. In bulk-transfected EA cells, overexpression of NFATp similarly extinguished expression of the Type II and Type X collagen genes and the CDMP-1 gene as compared to control vector (Rep) transfectants.

The level of expression of NFATp controls the extent to which a cell manifests a cartilage phenotype as determined by expression of markers characteristic of differentiated cartilage.

NFATp has the Features of a Murine Tumor Suppressor Gene

Several pieces of data suggest that the proliferating cartilage cells in NFATp-deficient animals may sometimes undergo transformation. Primitive transformed proliferating cells show early differentiation into chondroblasts. Columns of primitive transformed cells differentiating into prechondroblasts were also visible. High power of one year old NFATp−/− mouse showed cartilage cells invading muscle. High power of articular cartilage of one year old NFATp−/− mouse showed abnormal looking cartilage cells with multiple nuclei. The normal appearance of the layer of calcified cartilage was noted. High power examination of extra-articular cartilage cells from one year old NFATp−/− mouse showed multiple cells in clusters. Cells with multiple nucleoli were also visible.

The proliferating cartilage cells both in articular cartilage and in the extra-articular soft tissues varied in size but were usually very large, had increased chromatin content, noticeable mitotic figures and were safranin O positive. Cells with multiple nucleoli were observed. Further, this uncontrolled formation of extra-articular cartilage and bone often invaded and extended beyond the connective tissues, progressing between the overlying muscle fibers. This cytogenetic picture coupled with the invasion of the acetabulum by proliferating cartilage cells in the ligamentum teres strongly suggested a malignant process, likely accounting for the destruction of the joint in the older animals. Second, in contrast to the slow growth of cartilage cells observed in cultures established from wt and heterozygous mice, some of the cultures established from both the articular and extra-articular sites from NFATp−/− mice expanded rapidly, necessitating frequent passaging.

Thus, in contrast to wt cartilage cells, NFATp−/− cartilage cells did not display contact-induced growth inhibition since they continued to proliferate in vitro even when plated at confluency. Varying numbers of wt or NFATp−/− cartilage cells were plated and cell division monitored. Cell division continued even in cells that had reached confluency. Aneuploidy in NFATp−/− tumor cells was also seen. Karyotypic analysis of four tumor cell lines from NFATp−/− mice revealed aneuploidy in three of them. The first line was a normal male with random chromosome loss. The second line had a modal chromosome number of 40 in 7 cells with monosomy of chromosomes 4 and 12, trisomy of chromosome 17 and gain of markers in most of the cells. An additional 3 cells displayed additional structures and numerical abnormalities. Two clones were observed in the third tumor, a normal 40XX clone in 41 cells and an abnormal clone that demonstrated clonal evolution. A marker chromosome was observed in all cells in the clone, and in addition, 5 cells demonstrated loss of an X and 2 of these also had loss of chromosome 14. The fourth tumor, dervied from extra-articular cartilage, was pseudotetraploid with a modal chromosome number of 71–76 (range 71–89), with a consistent finding of loss of chromosomes 4 and 16. One to 6 marker chromosomes were observed in most cells and there were no normal diploid or tetraploid cells. (Table 1). Third, karyotypic analysis of four cartilage cell lines (one male, three female) established from NFATp–/– mice revealed aneuploidy in the three female lines, although there were no consistent karyotypic abnormalities observed. The histologic phenotype coupled with the loss of contact inhibition and the presence of aneuploidy suggests that the cartilage cells arising in NFATp deficient mice may occasionally undergo transformation to a malignant state. Some of the cartilage tumors in the NFATp–/– mice may thus be best classified as chondrosarcomas even though a pathologic survey of lungs, brain and intestine did not reveal metastatic lesions. However, spontaneous solid tumors in mice rarely metastasize. It should be noted also that NFATp–/– cartilage cells do retain a differentiated phenotype similar to some, but not all, human chondrosarcomas ("low grade").

Discussion

The NFATp Transcription Factor is a Regulator of Chondrogenesis

The data presented in this example show that levels of NFATp exquisitely control cartilage cell induction and proliferation, resulting in a spectrum of growth abnormalities ranging from hyperproliferation to frank transformation. Few molecular regulators of chondrogenesis are known, and most of these operate during skeletal morphogenesis rather than in the adult animal. Our studies demonstrate that a member of the NFAT family of transcription factors, NFATp, is a repressor of cartilage cell growth and differentiation in the adult animal. Further, the uncontrolled induction and proliferation of cartilage cells that results from its absence presumably increases the likelihood of a "second-hit" that then can result in frank transformation of these cells. To our knowledge, NFATp is the first transcription factor to be identified that controls the induction of chondrogenesis from adult connective tissue progenitor cells. There are three other known members of the NFAT family, all of which are expressed in cartilage. While all four known NFAT family members are present in cartilage cells, only the expression of NFATp is regulated during the process of chondrogenesis. Further, only the expression of NFATp and not NFATc, NFAT4 or NFAT3 was restricted to mesenchymal stem cells undergoing chondrogenesis rather than osteogenesis.

NFATp Regulates Chondrogenesis in the Adult Animal

Consistent with the normal skeletal development of mice lacking NFATp, NFATp expression was not detected in cartilage during embryogenesis. Rather, our data implicate NFATp as a critical regulator of chondrogenesis in the adult animal. Thus, NFATp expression is specifically regulated in human adult mesenchymal stem cells during in vitro chondrogenesis while overexpression of NFATp represses the mature cartilage phenotype.

This is in contrast to the function of the cartilage-specific transcription factor Sox9, which is critical in cartilage morphogenesis (Zhou, G., et al. 1998. J. Biol. Chem. 273, 14989–14997.). Mutations in the Sox9 gene or in the Sox9 promoter are responsible for the human disease campomelic dysplasia (Meyer, J., et al. 1997. Human Molecular Genetics 6, 91–98.; Wunderle et al., 1998). Several additional regulators of chondrogenesis during embryonic development have been identified (Caplan, A. I. 1988. Ciba Found. Symp. 136, 3–21.; Erlebacher, A., et al. 1995 Cell 80, 371–378., Poole, A. R. 1991 In "Cartilage: Molecular Aspects." B. K. Hall and S. A. Newman, eds. (Boca Raton: CRC Press), pp. 179–211.). Analysis of mutant mice has provided evidence for a role in cartilage development and differentiation for Indian Hedgehog (Vortkamp, A., et al. 1996. Science 273, 613–622.; Bitgood, M. J. and McMahon, A. P. 1995. Dev. Biol. 172, 126–38.), PTH Related protein (PTHrP) (Karaplis, A. C., et al. 1994 Genes Dev. 8, 277–289.; Vortkamp, A., et al. 1996. Science 273, 613–622.; Chung, U., et al. 1998). The parathyroid hormone/parathyroid hormone-related peptide receptor coordinates endochondral bone development by directly controlling chondrocyte differentiation. Proc. Natl. Acad. Sci. USA 95, 13030–13035.), FGFs (Deng, C., et al. 1996. Cell 84, 911–921.; Rousseau, F., et al. 1994. Nature 371, 252–254.; Shiang, R., et al. 1994. Cell 78, 335–342.), IGFs (Baker, J., et al. 1993. Cell 75, 73–82.), Noggin (Brunet, L. J., et al. 1998). Science 280, 1455–1457.) and bone morphogenetic proteins (BMPs), a family of secreted signaling molecules originally isolated by virtue of their ability to induce ectopic cartilage and endochondral bone formation when implanted into subcutaneous tissues of adult animals (Wozney, J. M., et al. 1988. Science 242, 1528–1534.; Vukicevic, S., Luyten, F. P., and Reddi, A. H. (1989). Stimulation of the expression of osteogenic and chondrogenic phenotypes in vitro by osteogenin. Proc. Natl. Acad. Sci. USA 86, 8793–8797.; Kingsley, D. M. (1994). Genes Dev. 8, 133–146.; Bitgood, M. J. and McMahon, A. P. 1995. Dev. Biol. 172, 126–38; Erlacher, L., et al. 1998. J. Bone & Miner. Research 13, 383–392.; Chang, S. C., et al. 1994. J. Biol. Chem. 269, 28227–28234.; Joyce, M. E., et al. 1990. J. Cell Biol. 110, 2195–2207.). It is unlikely that NFATp acts through controlling these known regulators of chondrogenesis since these appear to play a more important function in morphogenesis that affects both skeletal and non-skeletal organ systems than they do in controlling growth of adult cartilage cells. For example, the mouse short-ear mutation is secondary to inactivation of the BMP5 gene (Kingsley, D. M. 1994. Genes Dev. 8, 133–146.) while mutations of the GDF5 gene account for limb alterations in brachypodism mice (Storm, E. E., et al. 1994. Nature 368, 639–643). Indian hedgehog is expressed in prehypertrophic chondrocytes where it controls the rate of hypertrophic differentiation in part through inducing the expression of a second signal, PTHrP, in the perichondrium. PTHrP–/– mice have defects in formation of hypertrophic cartilage (Vortkamp, A., et al. 1996. Science 273, 613–622.; Chung, U., et al. 1998. Proc. Natl. Acad. Sci. USA 95, 13030–13035.). Indeed no evidence that NFATp directly regulates the transcription of several members of the BMP family or the TGFβ proteins themselves or acted through a secreted factor was found. Rather, the dysregulation of cartilage growth appeared to be cell-intrinsic. It is of interest, however, that NFATc and the type III TGF-β receptor are both required for endocardial cell transformation in the heart (Brown, C. B., et al. 1999. Science 283, 2080–2082.; Ranger, A. M., et al. 1998. Nature 392, 186–190.; Luis de la Pompa, J., et al. 1998. Nature 392, 182–186.), raising the possibility that signal transduction pathways stemming from TGF-β receptors intersect with NFAT proteins.

Initiation of chondrogenesis results in activation of NFATp that then sets in motion a genetic program to control cartilage differentiation and proliferation. These data indicate that NFATp-regulated genes in cartilage must act in part to repress this program since overexpression of NFATp extinguished the differentiated cartilage phenotype while loss of NFATp resulted in spontaneous activation of chondrogenesis. Future experiments will focus on identifying the upstream targets and downstream effectors of NFATp both in the mesenchymal stem cell and in mature articular cartilage. These data indicate that some of the NFATp-regulated genes in mesenchymal stem cells will control proliferation as evidenced by the uncontrolled division of these cells in its absence. Some of these may well be modifiers of NFATp activity that can account for the substantial sex difference in the development of the phenotype. Of interest, genetic modifier genes appear to play a role in the development of the phenotype; the phenotype described herein is not present in an independently generated NFATp-deficient strain which is a true null allele (Xanthoudakis, S., et al. 1996. Science 272, 892–895.). The NFATp-/- strains used herein are on the BALB/c and B10.D2 backgrounds while the other NFATp-/- strain has been bred onto a mixed 129/Sv/C57B1/6 background.

NFATp Controls Differentiation of Mesenchymal Stem Cells into Cartilage

NFATp acts as a repressor of cartilage cell differentiation from primitive mesenchymal stem cells since in its absence, cartilage cells, many of which undergo the endochondral sequence of ossification, are induced to form and proliferate in the surrounding extra-articular connective tissues. Thus, the developmental sequence of endochondral bone formation is recapitulated in the absence of NFATp. It has been difficult to recapitulate the process of chondrogenesis from stem cells in vitro although there has been some recent success in doing so under very stringent culture conditions (Johnstone, B., et al. 1998. Exp. Cell Res. 238, 265–272.; Mackay, A. M., et al. 1998 Tissue Engineering 4, 415–427.; Lennon, D. P., et al. 1996. In Vitro Cell. Dev. Biol. 32, 602–611.; Pittenger, M. F., et al. 1999. Science 284, 143–147.). Given these results, it will be to determine whether NFATp-/- mesenchymal stem cells derived from mice that also express an SV40 T antigen transgene (H-2Kb-tsA58 "Immortomouse") Jat, P. S., et al. 1991. Proc. Natl. Acad. Sci. USA 88, 5096–5100.; Dennis, J. E. and Caplan, A. I. 1996. J. Cell. Physiol. 167, 523–538.) will spontaneously differentiate into cartilage in vitro. Towards this end, the effect of the NFAT inhibitors, CsA and FK506, on in vitro chondrogenesis from wildtype mesenchymal stem cells can be tested. Compounds that block the fimction of NFATp in cartilage may prove valuable in achieving sustained differentiation and growth of cartilage from mesenchymal stem cells in vitro or in vivo. Such inhibitors might control mesenchymal stem cell recruitment and chondrogenesis in response to environmental injuries such as occur during normal mechanical wear and tear. NFATp inhibitors can also be used in degenerative joint diseases such as osteoarthritis, where cartilage has been destroyed, as well as in the stimulation of endochondral bone formation to repair bone defects and fractures in which endochondral bone formation plays an important role.

NFATp Acts as a Tumor Suppressor in Cartilage

NFATp displays properties of a tumor suppressor gene in cartilage as evidenced by the malignant transformation of NFATp-/- cells in both articular cartilage and in extra-articular cartilage. The invasive nature of the cartilage cell proliferation in vivo coupled with their behavior in vitro and ability to form tumors in syngeneic mice (LCG, unpublished observations) suggests that these are chondrosarcomas. There has been controversy about what constitutes malignancy in cartilage tumors in humans (Lee, F. Y., et al. 1999. Journal of Bone and Joint Surgery 81, 326–338). Chondrosarcomas are second only to osteosarcomas as the most frequent primary malignant tumors of bone (Enneking, W. F. 1986. Clin. Orthop. 204, 9–24.; (Lee, F. Y., et al. 1999. Journal of Bone and Joint Surgery 81, 326–338). Unlike osteosarcoma or Ewing's sarcoma, chondrosarcomas are minimally responsive to chemotherapy and are largely treated by surgical excision. Outcome is difficult to predict in part because chondrosarcomas are difficult to grade and can be confused with benign enchondroma or osteocartilaginous exostosis (Enneking, W. F. 1986. Clin. Orthop. 204, 9–24.; Lee, F. Y., et al. 1999. Journal of Bone and Joint Surgery 81, 326–338). This has recently prompted the use of other methods of assessing tumor virulence such as imaging, mean DNA content and presence of aneuploidy to help predict outcome (Helio, H., et al. 1995 Eur. J. Surg. Oncol. 21, 408–413.; Kreicbergs, A., et al.1980. Anal. Quant. Cytol. 4, 272–279.). Although a variety of chromosomal abnormalities have been noted in human chondrosarcomas, including loss of heterozygosity at the EXT1 locus (Sandberg, A. A. and Bridge, J. A. (1994). The cytogenetics of bone and soft tissue tumors (Austen, Tex.: R. G. Landes Company).; Raskind, W. H., et al. 1995. Am. J. Hum. Genet. 56, 1132–1139.), no consistent cytogenetic phenotype has been described, similar to what was observed in the NFATp-/- tumor lines. Unlike osteosarcoma and Ewing's sarcoma that almost always involve mutations in the Rb (Friend, S. H., et al. 1986 Nature 323, 643–646.) and EWS1 (Ewing's sarcoma) genes, no frequent association with known tumor suppressor genes has been reported for chondrosarcomas, although abnormalities in p53 expression have been reported (Dobashi, Y.,et al. 1993. Diagnostic Molecular Pathology 2(4), 257–263.; Wadayama, B., et al. 1993. Br. J. Cancer 68, 1134–1139.). In preliminary experiments abnormalities in p53 expression have not been detected, but it will be important to analyze the NFATp-/- transformed cell lines presented here for mutations in other known tumor suppressor genes. Further, since almost no transformed, differentiated, rapidly growing and transfectable cartilage cell lines are available, these cell lines should prove very valuable for the analysis of gene regulation and function in cartilage. Finally, our data suggest that a careful examination of human chondrosarcoma tissue for the presence of NFATp gene mutations may be warranted.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of identifying a compound that modulates cartilage growth or differentiation comprising:
   a) contacting cartilage cells from a mouse deficient in NFATp with a test compound; and
   b) determining the effect of the test compound on the growth and differentiation of the cartilage cells, the test compound being identified as a modulator of cartilage growth or differentiation based on the ability of the test compound to modulate the growth or differentiation of the cartilage cells from the mouse deficient in NFATp.

2. The method of claim 1, wherein the compound inhibits cartilage growth.

3. The method of claim 1, wherein the cartilage cells are in a NFATp deficient mouse and the cartilage cells are contacted with the test compound by administering the test compound to the NFATp deficient mouse.

4. The method of claim 1, wherein the cartilage cells are isolated from a NFATp deficient mouse and the cartilage cells are contacted with the test compound by culturing the test compound with the isolated cartilage cells deficient in NFATp.

5. A method of identifying a compound that modulates cartilage growth or differentiation, comprising
   a) providing an indicator composition comprising NFATp protein and a target molecule;
   b) contacting the indicator composition with each member of a library of test compounds;
   c) selecting from the library of test compounds a compound of interest that modulates the activity of NFATp protein; and
   d) determining the effect of the compound of interest on cartilage growth or differentiation in a cell to thereby identify a compound that modulates cartilage growth or differentiation.

6. A method of identifying a compound that modulates cartilage growth or differentiation, comprising
   a) providing an indicator composition comprising NFATp protein and a target molecule wherein the indicator composition is a cell that expresses NFATp protein;
   b) contacting the indicator composition with each member of a library of test compounds;

c) selecting from the library of test compounds a compound of interest that modulates the activity of NFATp protein; and d) determining the effect of the compound of interest on cartilage growth or differentiation in a cell to thereby identify a compound that modulates cartilage growth or differentiation.

7. A method of identifying a compound that modulates cartilage growth or differentiation, comprising a) providing an indicator composition comprising NFATp protein and a target molecule wherein the indicator composition is a cell that expresses NFATp protein and wherein the cell has been engineered to express the NFATp protein by introducing into the cell an expression vector encoding the NFATp protein;

b) contacting the indicator composition with each member of a library of test compounds;

c) selecting from the library of test compounds a compound of interest that modulates the activity of NFATp protein; and d) determining the effect of the compound of interest on cartilage growth or differentiation in a cell to thereby identify a compound that modulates cartilage growth or differentiation.

8. A method of identifying a compound that modulates cartilage growth or differentiation, comprising a) providing an indicator composition comprising NFATp protein and a target molecule wherein the indicator composition is a cell free composition;

b) contacting the indicator composition with each member of a library of test compounds;

c) selecting from the library of test compounds a compound of interest that modulates the activity of NFATp protein; and d) determining the effect of the compound of interest on cartilage growth or differentiation in a cell to thereby identify a compound that modulates cartilage growth or differentiation.

9. A method of identifying a compound that modulates cartilage growth or differentiation, comprising a) providing an indicator composition comprising NFATp protein, wherein the indicator composition is a cell that expresses an NFATp protein and a target molecule;

b) contacting the indicator composition with each member of a library of test compounds;

c) monitoring the ability of the test compound to modulate the interaction of the NFATp protein with a target molecule;

d) selecting from the library of test compounds a compound of interest that modulates the activity of NFATp protein; and e) determining the effect of the compound of interest on cartilage growth or differentiation in a cell to thereby identify a compound that modulates cartilage growth or differentiation.

10. A method of identifying a compound that modulates cartilage growth or differentiation, comprising a) providing an indicator composition comprising NFATp protein, wherein the indicator composition comprises an indicator cell, wherein the indicator cell comprises an NFATp protein and a reporter gene responsive to the NFATp protein;

b) contacting the indicator composition with each member of a library of test compounds;

c) selecting from the library of test compounds a compound of interest that modulates the activity of NFATp protein; and d) determining the effect of the compound of interest on cartilage growth or differentiation in a cell to thereby identify a compound that modulates cartilage growth or differentiation.

11. The method of claim 10, wherein said indicator cell contains: a recombinant expression vector encoding the NFATp protein; and a vector comprising an NFATp-responsive regulatory element operatively linked a reporter gene; and step b) further comprises determining the level of expression of the reporter gene in the indicator cell in the presence of the test compound; and wherein the selection of a compound of interest in step c) is carried out by comparing the level of expression of the reporter gene in the indicator cell in the presence of the test compound with the level of expression of the reporter gene in the indicator cell in the absence of the test compound.

12. A method of identifying a compound that modulates cartilage growth or differentiation, comprising a) contacting cartilage cells comprising NFATp protein and a target molecule with a test compound ex vivo; and b) measuring the activity of NFATp protein in the cartilage cells in the presence of the test compound and comparing with the activity of NFATp protein in the cartilage cells in the absence of the test compound to determine whether the test compound modulates activity of NFATp protein; and c) determining the effect of the test compound on cartilage growth or differentiation to thereby identify a compound that modulates cartilage growth or differentiation.

13. The method of claim 12, wherein the cartilage cells are mesenchymal stem cells.

14. The method of claim 12, wherein the cartilage cells are chondrosarcoma cells.

15. The method of claim 12, wherein the cartilage cells are chondroblasts.

16. The method of claim 12, wherein the cartilage cells are articular cartilage cells.

* * * * *

UNITED STATES PATENT AND TRADEMARK OFFICE
CERTIFICATE OF CORRECTION

PATENT NO.     : 6,548,734 B1
DATED          : April 15, 2003
INVENTOR(S)    : Laurie H. Glimcher et al.

It is certified that error appears in the above-identified patent and that said Letters Patent is hereby corrected as shown below:

<u>Column 54,</u>
Line 43, "d) determining the effect of the test compound on cartilage…" should read
-- c) determining the effect of the test compound on cartilage… --

Signed and Sealed this

Thirtieth Day of September, 2003

JAMES E. ROGAN
*Director of the United States Patent and Trademark Office*

SEQUENCE LISTING

<160> NUMBER OF SEQ ID NOS: 20

<210> SEQ ID NO 1
<211> LENGTH: 7
<212> TYPE: PRT
<213> ORGANISM: synthetic construct

<400> SEQUENCE: 1

Ser Pro Arg Ile Glu Ile Thr
 1               5

<210> SEQ ID NO 2
<211> LENGTH: 25
<212> TYPE: PRT
<213> ORGANISM: synthetic construct

<400> SEQUENCE: 2

Ala Lys Pro Ala Gly Ala Ser Gly Leu Ser Pro Arg Ile Glu Ile Thr
 1               5                  10                  15

Pro Ser His Glu Leu Ile Gln Ala Val
            20                  25

<210> SEQ ID NO 3
<211> LENGTH: 13
<212> TYPE: PRT
<213> ORGANISM: synthetic construct

<400> SEQUENCE: 3

Ser Gly Leu Ser Pro Arg Ile Glu Ile Thr Pro Ser His
 1               5                  10

<210> SEQ ID NO 4
<211> LENGTH: 9
<212> TYPE: PRT
<213> ORGANISM: synthetic construct

<400> SEQUENCE: 4

Ser Pro Ala Ile Ala Ile Ala Pro Ser
 1               5

<210> SEQ ID NO 5
<211> LENGTH: 24
<212> TYPE: DNA
<213> ORGANISM: synthetic construct

<400> SEQUENCE: 5
tctccaatca gtcgggctcc tatg                                      24

<210> SEQ ID NO 6
<211> LENGTH: 22
<212> TYPE: DNA
<213> ORGANISM: synthetic construct

<400> SEQUENCE: 6
gctcggggca gtctgttgtt gg                                        22

<210> SEQ ID NO 7
<211> LENGTH: 42
<212> TYPE: DNA
<213> ORGANISM: synthetic construct

<400> SEQUENCE: 7

-continued

```
tccggcgcat gcgagccgtc atcgactgtg ctgggatcct ga                              42

<210> SEQ ID NO 8
<211> LENGTH: 36
<212> TYPE: DNA
<213> ORGANISM: synthetic construct

<400> SEQUENCE: 8
ggacccgggt caattggcag gaaggtacgt gaaacg                                     36

<210> SEQ ID NO 9
<211> LENGTH: 22
<212> TYPE: DNA
<213> ORGANISM: synthetic construct

<400> SEQUENCE: 9
cttccccagc agcctctcat cc                                                    22

<210> SEQ ID NO 10
<211> LENGTH: 24
<212> TYPE: DNA
<213> ORGANISM: synthetic construct

<400> SEQUENCE: 10
ccgtggtggg caaaaggctc agtg                                                  24

<210> SEQ ID NO 11
<211> LENGTH: 22
<212> TYPE: DNA
<213> ORGANISM: synthetic construct

<400> SEQUENCE: 11
gaagctaccc tccggtacag ag                                                    22

<210> SEQ ID NO 12
<211> LENGTH: 21
<212> TYPE: DNA
<213> ORGANISM: synthetic construct

<400> SEQUENCE: 12
gcttcatagc tggctgtagc c                                                     21

<210> SEQ ID NO 13
<211> LENGTH: 21
<212> TYPE: DNA
<213> ORGANISM: synthetic construct

<400> SEQUENCE: 13
cctgtctgct tcttgtaaaa c                                                     21

<210> SEQ ID NO 14
<211> LENGTH: 19
<212> TYPE: DNA
<213> ORGANISM: synthetic construct

<400> SEQUENCE: 14
acagaggtgt ttgacacag                                                        19

<210> SEQ ID NO 15
<211> LENGTH: 21
<212> TYPE: DNA
<213> ORGANISM: synthetic construct

<400> SEQUENCE: 15
```

```
cttctcagga ttcctagtgg c                                              21

<210> SEQ ID NO 16
<211> LENGTH: 20
<212> TYPE: DNA
<213> ORGANISM: synthetic construct

<400> SEQUENCE: 16
gagccattga gtgatgcacc                                                20

<210> SEQ ID NO 17
<211> LENGTH: 20
<212> TYPE: DNA
<213> ORGANISM: synthetic construct

<400> SEQUENCE: 17
acgggacctg ttctttaatg                                                20

<210> SEQ ID NO 18
<211> LENGTH: 20
<212> TYPE: DNA
<213> ORGANISM: synthetic construct

<400> SEQUENCE: 18
cttatacacc acgttgttgg                                                20

<210> SEQ ID NO 19
<211> LENGTH: 20
<212> TYPE: DNA
<213> ORGANISM: synthetic construct

<400> SEQUENCE: 19
ctggagaaga gctatgagct                                                20

<210> SEQ ID NO 20
<211> LENGTH: 20
<212> TYPE: DNA
<213> ORGANISM: synthetic construct

<400> SEQUENCE: 20
gccatgccaa tgttgtctct                                                20
```